(12) United States Patent
Phalipon et al.

(10) Patent No.: US 6,528,061 B1
(45) Date of Patent: Mar. 4, 2003

(54) IMMUNOGENIC POLYPEPTIDES THAT MIMIC A SURFACE POLYSACCHARIDE ANTIGEN OF A PATHOGENIC MICROORGANISM, METHOD FOR OBTAINING THE SAME, AND THEIR USE IN VACCINE COMPOSITIONS

(76) Inventors: Armelle Phalipon, 208, rue de Vaugirard, 75015 Paris (FR); Philippe Sansonetti, 131, boulevard Brune, 75014 Paris (FR); Franco Felici, viale B. Rizzieri 247, 00173 Roma (IT); Riccardo Cortese, Via M. Massimo 16, 00144 Roma (IT); Jean Pierre Kraehenbuhl, Sur la Croix, CH 1812, Rivaz (CH)

( * ) Notice: Subject to any disclaimer, the term of this patent is extended or adjusted under 35 U.S.C. 154(b) by 0 days.

(21) Appl. No.: 09/144,280

(22) Filed: Aug. 31, 1998

Related U.S. Application Data

(60) Provisional application No. 60/057,906, filed on Sep. 4, 1997.

(51) Int. Cl.[7] ...................... A01N 63/00; A61K 39/395; A61K 39/00; A61K 39/02; C12P 21/04
(52) U.S. Cl. ................... 424/190.1; 424/93.48; 424/141.1; 424/184.1; 424/190.1; 424/234.1; 435/70.21; 435/71.1; 530/388.2; 530/388.4; 530/389.5; 530/300
(58) Field of Search ........................ 424/175.1, 176.1, 424/178.1, 183.1, 184.1, 185.1, 278.1; 435/7.93, 7.94, 7.95, 339–340, 341, 342, 345, 971; 436/507, 518, 537, 540; 530/388.9

(56) References Cited

PUBLICATIONS

Folgori et al. 1994. The EMBO Journal vol. 13 (9): 2236–2243.*
Astori et al. 1996. Molecular Immunology. 33(13):1017–1024.*
Dromer et al. 1987. Infection and Immunity. 55(3): 749–752.*
Lett et al. 1995. Infection and Immunity. 63(7): 2645–2651.*
Mecchia et al. 1996. Journal of Immunology. 157(8): 3726–3736.*
Prezzi et al. 1996. Journal of Immunology. 156(11): 4504–4513.*
Sanford et al. Infection and Immunity. 58(6): 1919–1923, 1990.*
Phalipon et al. 1995. Journal of Experimental Medicine. 182: 769–778.*
Phalipon et al. 1997. European Journal of Immunology. 1997. 27: 2620–2625.*
Valadon et al. 1996. JMB. 261(1): 11–22.*
Valadon et al., "Peptide Libraries Define the Fine Specificity of Anti–polysaccharide Antibodies To *Cryptoccus Neoformans*," *J. Microbiology*, vol. 261, No. 1, pp. 11–22 (1996).
Phalipon et al., "Monoclonal Immunoglobulin A Antibody Directed Against Serotype–specific Epitope of *Shigella flexneri* Lipopolysaccharide Protects Against Murine Experimental Shigellosis," *J. Exp. Med.*, vol. 182, No. 3 (Sep. 1, 1995).

* cited by examiner

Primary Examiner—Nita Minnifield
Assistant Examiner—JaNa Hines
(74) Attorney, Agent, or Firm—Finnegan, Henderson, Farabow, Garrett & Dunner, L.L.P.

(57) ABSTRACT

A purified immunogenic polypeptide comprises an epitope unit recognized by a protective monoclonal antibody having a high affinity and a high specificity for a surface polysaccharide of a pathogenic microorganism of bacterial, viral, or fungal origin. The polypeptide is capable of inducing an immune response in vivo against the pathogenic microorganism. The immune response confers protection in mice against challenge with the virulent microorganisms.

2 Claims, 7 Drawing Sheets

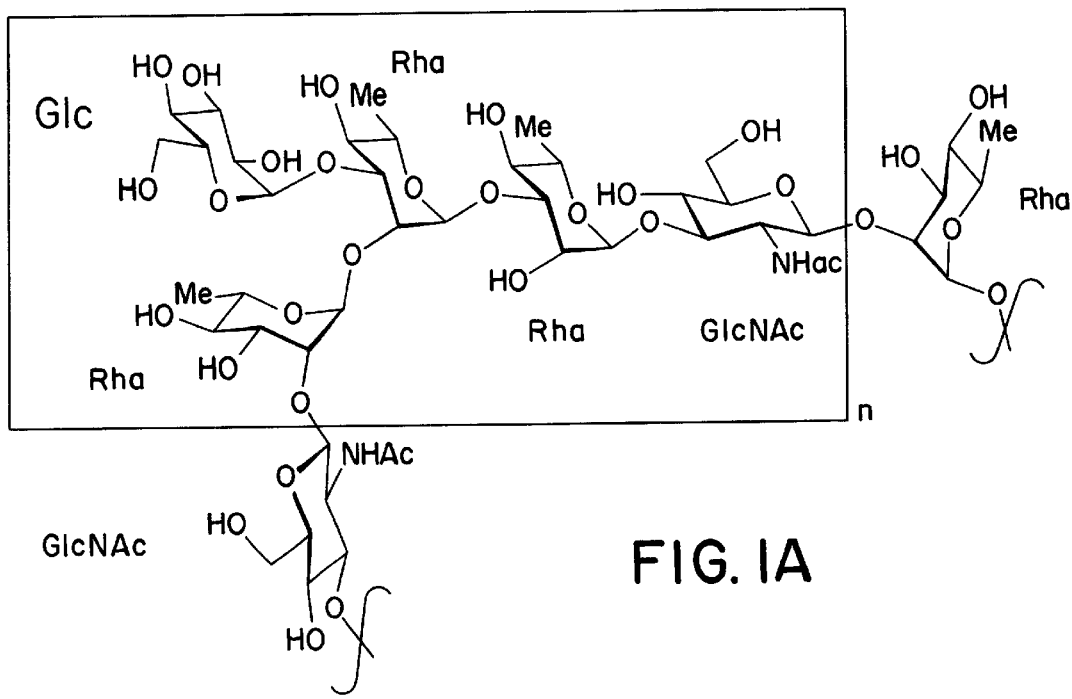
FIG. IA
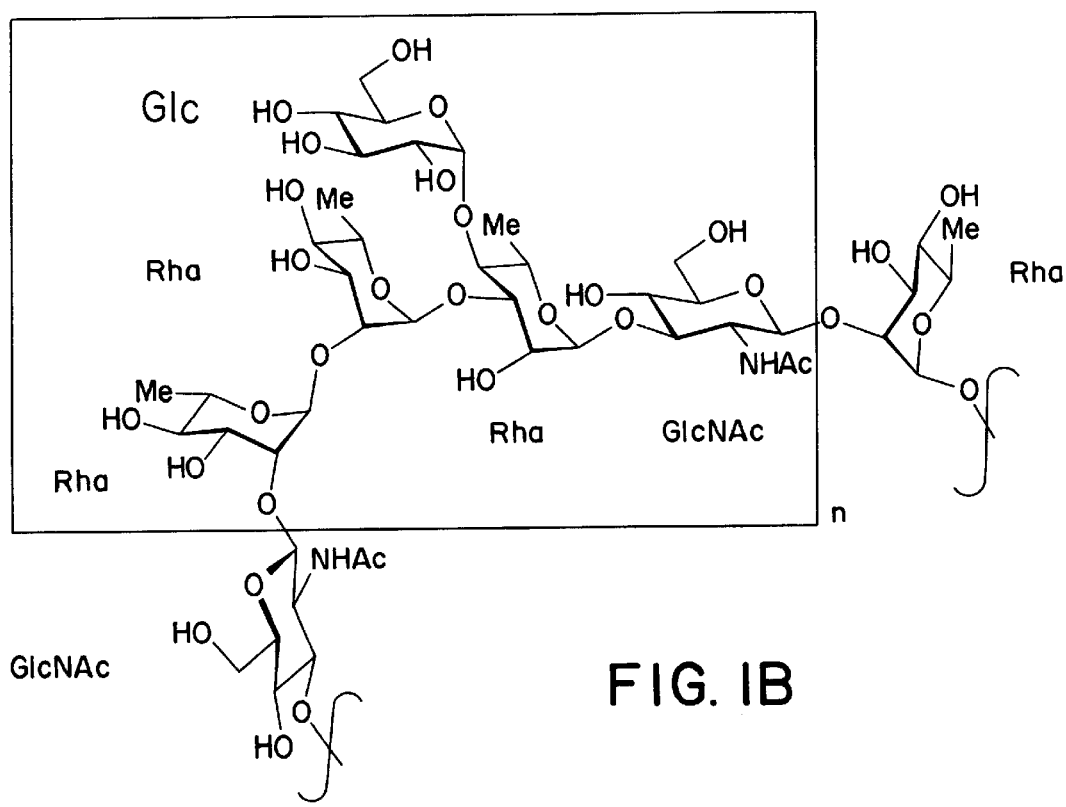
FIG. IB 1  2

1  2

1  2

1  2

| clone | peptide sequence | recognition by mIgA I3 | recognition by mIgA C5 |
|---|---|---|---|
| 100c | YKPLGALTH (SEQ ID NO:1) | 0.85 | 0.05 |
| 121 | KVPAWARRL (SEQ ID NO:3) | 0.18 | 0.51 |
| 6 | HIPAYATHV (SEQ ID NO:4) | 0.05 | 1.40 |
| 115 | KVPPWAATA (SEQ ID NO:2) | 0.51 | 1.36 |
| 19 | EHFWEQRPR (SEQ ID NO:5) | 0.06 | 1.11 |
| 5c | TRGHFLQNR (SEQ ID NO:6) | 0.05 | 1.79 |
| 12 | HYLVQSPPW (SEQ ID NO:7) | 0.05 | 1.14 |
| 21 | QSHFLLQGT (SEQ ID NO:8) | 0.05 | 1.12 |
| 22 | KRHFLSQRQ (SEQ ID NO:9) | 0.06 | 1.23 |
| 11c | RRHFLDQRG (SEQ ID NO:10) | 0.05 | 1.92 |
| 20 | HFLSQNFFG (SEQ ID NO:11) | 0.05 | 1.66 |
| 18c | SPHFFNQIR (SEQ ID NO:12) | 0.06 | 1.26 |
| 16 | WGPFQYAAG (SEQ ID NO:13) | 0.05 | 1.98 |
| 148c | SQGRWPPWR (SEQ ID NO:14) | 0.31 | 0.66 |
| 8 | LLRQARERP (SEQ ID NO:15) | 0.05 | 0.96 |
| 160c | GSPLRQRRS (SEQ ID NO:16) | 0.20 | 0.36 |
| 143c | GSPLRQRSL (SEQ ID NO:17) | 0.19 | 0.50 |
| 14 | PPLSQRRAL (SEQ ID NO:18) | 0.05 | 1.46 |
| 9 | TRQQNNPER (SEQ ID NO:19) | 0.05 | 0.90 |
| pwt | | 0.05 | 0.05 |

FIG. 5

SEQUENCE LISTING

<160> NUMBER OF SEQ ID NOS: 19

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms
<220> FEATURE:
<223> OTHER INFORMATION: This peptide contains sequences wherein the
      cysteine at positions 1 and/or 11 may replaced by a hydrogen atom

<400> SEQUENCE: 1

Cys Tyr Lys Pro Leu Gly Ala Leu Thr His Cys
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 2

Lys Val Pro Pro Trp Ala Ala Thr Ala
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 3

Lys Val Pro Ala Trp Ala Arg Arg Leu
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 4

His Ile Pro Ala Tyr Ala Thr His Val
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 5

```
Glu His Phe Trp Glu Gln Arg Pro Arg
  1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 6

Thr Arg Gly His Phe Leu Gln Asn Arg
  1               5
```

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 7

His Tyr Leu Val Gln Ser Pro Pro Trp
  1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 8

Gln Ser His Phe Leu Leu Gln Gly Thr
  1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 9

Lys Arg His Phe Leu Ser Gln Arg Gln
  1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 10

Arg Arg His Phe Leu Asp Gln Arg Gly
  1               5
```

```
<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 11

His Phe Leu Ser Gln Asn Phe Phe Gly
  1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 12

Ser Pro His Phe Phe Asn Gln Ile Arg
  1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 13

Trp Gly Pro Phe Gln Tyr Ala Ala Gly
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 14

Ser Gln Gly Arg Trp Pro Pro Trp Arg
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 15

Leu Leu Arg Gln Ala Arg Glu Arg Pro
  1               5

<210> SEQ ID NO 16
<211> LENGTH: 9
<212> TYPE: PRT
<213> ORGANISM: Artificial Sequence
```

-continued

```
<220> FEATURE:
<223> OTHER INFORMATION: Description of Artificial Sequence: synthetic
      peptide used to induce an immune response against
      pathogenic microorganisms

<400> SEQUENCE: 16

Gly Ser Pro Leu Arg Gln Arg Arg Ser
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 17

Gly Ser Pro Leu Arg Gln Arg Ser Leu
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 18

Pro Pro Leu Ser Gln Arg Arg Ala Leu
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: synthetic
      peptide used to induce an immune response against
      pathogenic microorganisms

<400> SEQUENCE: 19

Thr Arg Gln Gln Asn Asn Pro Glu Arg
 1               5
```

IMMUNOGENIC POLYPEPTIDES THAT MIMIC A SURFACE POLYSACCHARIDE ANTIGEN OF A PATHOGENIC MICROORGANISM, METHOD FOR OBTAINING THE SAME, AND THEIR USE IN VACCINE COMPOSITIONS

CROSS-REFERENCE TO RELATED APPLICATION

This application hereby claims the benefit under 35 U.S.C. §119(e) of United States provisional application Ser. No. 60/057,906 filed Sep. 4, 1997. The entire disclosure of this application is relied upon and incorporated by reference herein.

BACKGROUND OF THE INVENTION (i) Field of the Invention

The present invention pertains to immunogenic polypeptides, which comprise at least an epitope recognized by a protective monoclonal antibody having a high affinity and a high specificity for a surface polysaccharide of a pathogenic microorganism. The polypeptides induce an immune response in vivo against the pathogenic microorganism. The invention also relates to methods for selecting such immunogenic polypeptides, and also immunogenic or vaccinal compositions containing the polypeptides.

(ii) Description of the Related Art

Throughout this application various references are referred to within parentheses. Disclosures of these publications in their entireties are hereby incorporated by reference into this application to more fully describe the state of the art to which this invention pertains.

Polysaccharide molecules have been shown to be present at the surface of numerous pathogenic microorganisms. Some of these polysaccharide molecules have been depicted to protect the infecting pathogenic organism from the immune system of the infected mammalian host.

The initial immunologic response to administration of a capsular polysaccharide is the production of antibodies of the IgM class, which persist for relatively short periods (Beuvery et al., 1982; Beuvery et al., 1983). A similar response is manifested after the same capsular antigen is injected a second time (Käyhty et al., 1984). Absence of a booster response indicates the lack of "immunologic memory", attributes of a thymus-independent antigen.

The production of polysaccharides by bacteria has been recognized for a long time and a number of bacteria, including pneumococci, streptococci, staphylococci, menigococci, ASalmonella, Shigella, *Haemophilus influenza, Escherichia coli, Kilebsiella pneumoniae* and *Bacteroides fragilis*, are frequent causes of illness in man.

The bacterial cell wall is not the sole pathogenic organism component that contains polysaccharide antigens that are considered important determinants for inducing an immune response. A lot of viruses, such as rotaviruses (Hoshino et al., 1994), parainfluenza viruses (Ray et al., 1986; Tsurudome et al., 1989, Henrickson, 1991; Kasel et al., 1984), influenza viruses (Murphy et al., 1990; Tamura et al., 1996; Ada et al., 1986; Tamura et al., 1990; Tamura et al., 1991) or immunodeficiency viruses (FIV, HIV etc.) and fungi also express polysaccharide antigens at their surface, notably under the form of highly glycosylated proteins.

Immunodeficiency viruses, like FIV or HIV, all express envelope glycoproteins (gp 120 for HIV-1, gp 125 for HIV-2) at their surfaces. These envelope glycoproteins have been shown to be deeply involved in virus entry into target cells of the host, specifically the V3 loop domain of these external glycoproteins.

Pathogenic fungi, like some strains of *Candida albicans* or *Neurospora crassa*, also express polysaccharide antigenic determinants involved in the immune response of the host (Reiss, 1986).

The main targets of the protective immune response against bacterial infection are the capsular polysaccharide as well as the O—Ag carbohydrate moiety of the LPS (for a review, see Austrian, 1985). Carbohydrate antigens are T-cell independent, inducing weak antibody responses associated with the lack of a strong B cell memory response (Bondada et al., 1994). Vaccine strategies have thus been mainly focused on the development of either polysaccharide-protein conjugates or anti-idiotype vaccines based on mimicking the carbohydrate structure (Lucas, 1994). The difficult steps of the former approach are the purification of the polysaccharide (especially-when starting from LPS, which must be devoid of any residual lipid A-related endotoxic activity), and the loss of immunogenicity of the carbohydrate moiety during coupling to the protein carrier. Carbohydrate synthesis may diminish the problems associated with antigen purification, but nonetheless remains a limited solution due to the overall difficulties of carbohydrate chemistry.

The fact that the surface polysaccharide antigens of pathogenic microorganisms, and in particular the antigenic capsular polysaccharide of bacteria, seem to induce predominantly a T cell independent immune response renders these isolated or chemically synthesized antigens less valuable to use for inducing a protective immune response in the infected host.

Moreover, the synthesis of such polysaccharide antigen molecules at an industrial and commercial scale is difficult and very costly as compared with the synthesis of protein and peptide antigen compounds that are the active principals of the conventional vaccine compositions.

Thus, there is a need in the art to design protein or peptide molecules that are able to immunologically mimic the antigenic polysaccharide, specifically that are able to induce a strong and protective immune response to the corresponding pathogenic organism.

One strategy, based on the mimicry of carbohydrate antigens by anti-idiotype antibodies, is not a simple alternative to the use of the polysaccharide antigen itself, since obtaining these antibodies is relatively time-consuming, and their use in humans is still a matter of debate. Therefore, polysaccharide-protein conjugates remain, despite difficulties, the only viable strategy for human vaccination against bacterial polysaccharidic antigens investigated until now.

As the anti-idiotype antibody molecule in its entirety is unsuitable for repeated immunization, the characterization and use of its CDRs as immunogenic peptides to elicit anti-carbohydrate antibodies has recently been reported (Weternick et al., 1995), representing an additional complication. In comparison, obtaining peptide mimics using phage display technology is quite straightforward.

Over the last few years phage-displayed peptide libraries have been widely screened with antibodies as well as non-antibody molecules leading to the identification of new ligands that do not necessarily resemble the natural ones, but display similar binding capacity (for reviews see Scott et al., 1994; Cortese et al., 1995; Felici et al., 1995; Daniels et al., 1996).

The identification of peptides that mimic carbohydrate structures has also been reported (Oldenburg et al., 1992; Scott et al., 1992, Hoess et al., 1993, Bianchi et al., 1995; Bonnycastle et al., 1996; Valadon et al., 1996). This approach might be an alternative to the use of anti-idiotypic antibodies as mimics (Westerinck et al., 1995).

In particular, Valadon et al (1996) have used phage-displayed hexa- or deca-peptide libraries in order to select peptides binding to a monoclonal antibody, Mab 2H1, directed against the glucuronoxylomannan (GXM) capsular polysaccharide from *Cryptococcus neoformans*. These authors have selected about 35 different peptides that bind to the 2H1 anti-GXM monoclonal antibody. These peptides gathered in four different motifs, the peptides belonging to one specific motif exhibiting a significant homology (Tables 1 and 3). Further, these authors have immunized mice with some of the selected peptides (namely PA1, P601E, and P514), but have elicited only a small anti-GXM response, although they have stimulated the production of antibodies that have the 2H1 idiotype (unpublished results of the authors). There is no need to say that Valadon et al., in failing to obtain antibodies to the initial polysaccharide antigen with the selected hexa- or deca-peptides, have also failed to obtain any protective antibody against glucuronoxylomannan of *Cryptococcus neoformans*.

One explanation for the failure of Valadon et al. to select random peptides inducing a significant immune response against glucuronoxylomannan of *C. neoformans* lies probably in the weak specificity of the initial anti-GXM monoclonal antibody (2H1) used by these authors, which did not confer good selectivity properties in the screening steps of the candidate peptides expressed by the phage clones of the hexa- or decapeptide libraries, although this particular point is not discussed in Valadon et al.'s article. The weak specificity of the 2H1 monoclonal antibody used by Valadon et al. may be deduced from the fact that three to four rounds of selection screening has been necessary in order to select clones expressing candidate peptide mimics.

Thus, the immunogenicity of phage-displayed peptides that mimic the carbohydrate structures involved in the protective immune response against pathogens has not been reported so far. Consequently, the availability of carbohydrate peptide mimics that are able to induce a protective immune response against a pathogenic organism is a goal that had, to date, never been reached.

SUMMARY OF THE INVENTION

Consequently, the present inventors have investigated whether random peptides selected through such a strategy could act as immunogenic mimics able to induce anti-carbohydrate antibodies. The pathogen *S. flexneri* has been selected as a particular embodiment of the present invention, although it will be understood that the invention is not limited to this embodiment.

The inventors have recently reported that a monoclonal antibody of the IgA type directed against a serotype-specific epitope of the O—Ag, mIgA C5, and present in local secretions before infection, confers protection, thus showing the fundamental role played by both the carbohydrate O—Ag (especially the serotype-specific determinants) and the local humoral response against this pathogen (Phalipon et al., 1995).

More particularly, the illustrative embodiment of this invention is based on the repeated saccharidic unit of the O—Ag of *S. flexneri*. The structure of this saccharidic unit is shown in FIG. 1.

With reference to FIG. 1, the repeated saccharidic unit of serotype 5a is shown in FIG. 1(a) and the repeated saccharidic unit of serotype 2A is shown in FIG. 1(b). The saccharidic unit is surrounded, and "n" indicates that it is repeated n times to constitute the O—Ag. The GlcNAc and Rha residues outside the surrounding are part of the (n-1) and (n+1) units, respectively.

Using the mIgA C5 monoclonal antibody as well as the monoclonal antibody mIgA I3, both specific for the O-antigen (O—Ag) part of the human pathogen *Shigella flexneri* serotype 5a LPS and both protective against homologous infection, two phage-displayed nonapeptide libraries were screened in order to select specific random peptides that are recognized with a high specificity and a high affinity by the monoclonal antibodies. The random peptides were found to be capable of inducing a protective immune response to the pathogen in animals, specifically in mice.

These results are the first example of immunogenic mimicry of carbohydrates by phage-displayed peptides. Immunization of mice with one of the mimotopes can confer protection against subsequent infection. Therefore, the results indicate a new technique for the development of anti-polysaccharide vaccines.

Thus, the present invention provides an immunogenic polypeptide, which comprises an epitope recognized by a protective monoclonal antibody having a high affinity and a high specificity for a surface polysaccharide of a pathogenic microorganism. The polypeptide induces an immune response in vivo against the pathogenic organism. More particularly, the immunogenic peptide of the invention defined herein induces a protective humoral and/or cellular immune response against the pathogenic organism.

This invention also provides a purified polynucleotide coding for an immunogenic polypeptide as defined herein.

The invention is also directed to a method for selecting an immunogenic polypeptide as defined herein, comprising selecting, among a random peptide library, pertinent peptides that bind with a high affinity to a specifically chosen monoclonal antibody directed against a surface polysaccharide of a pathogenic microorganism, then characterizing the selected polypeptide(s) and ensuring that the selected polypeptide(s) induce a protective immune response in a mammal host against the pathogenic microorganism.

The invention also provides an immunogenic composition comprising an immunogenic polypeptide or a purified polynucleotide according to the invention.

This invention also provides a polyclonal or a monoclonal antibody, which is directed against an immunogenic polypeptide according to the invention.

BRIEF DESCRIPTION OF THE DRAWINGS

This invention will be described in greater detail with reference to the drawings in which:

FIG. 1 depicts the structure of the repeated saccharidic unit of the O—Ag of *S. flexneri*. The serotype 5a (a) and serotype 2a (b) basic structures are shown. The saccharidic unit is surrounded and "n" indicates that it is repeated n times to constitute the O—Ag. The GlcNAc and Rha residues outside the surrounding are part of the (n-1) and (n+1) unit, respectively.

FIG. 5 shows the phage-displayed nonapeptide sequences interacting with the antigen binding site of mIgA C5 and/or mIgA I3 specific for the O—Ag of S. flexneri serotype 5a.

The number of the phage clone and the corresponding sequence displayed by it are indicated. Recognition of these phage clones by mIgA C5 and/or mIgA I3 is indicated by the OD value obtained during screening of the nonapeptide libraries as described in Materials and Methods. Phage clones 100c, 121, 115, 148c, 160c, and 143c were selected using mIgA I3, pwt is the negative control (a phage containing wild type pVIII proteins), all the other clones were selected using mIgA C5. The letter "c" following the number of the clones indicated that these clones were selected from the cysteine-constrained nonapeptide library, thus in the pVIII recombinant protein the peptide insert is flanked by two cysteine residues.

Figure 6:
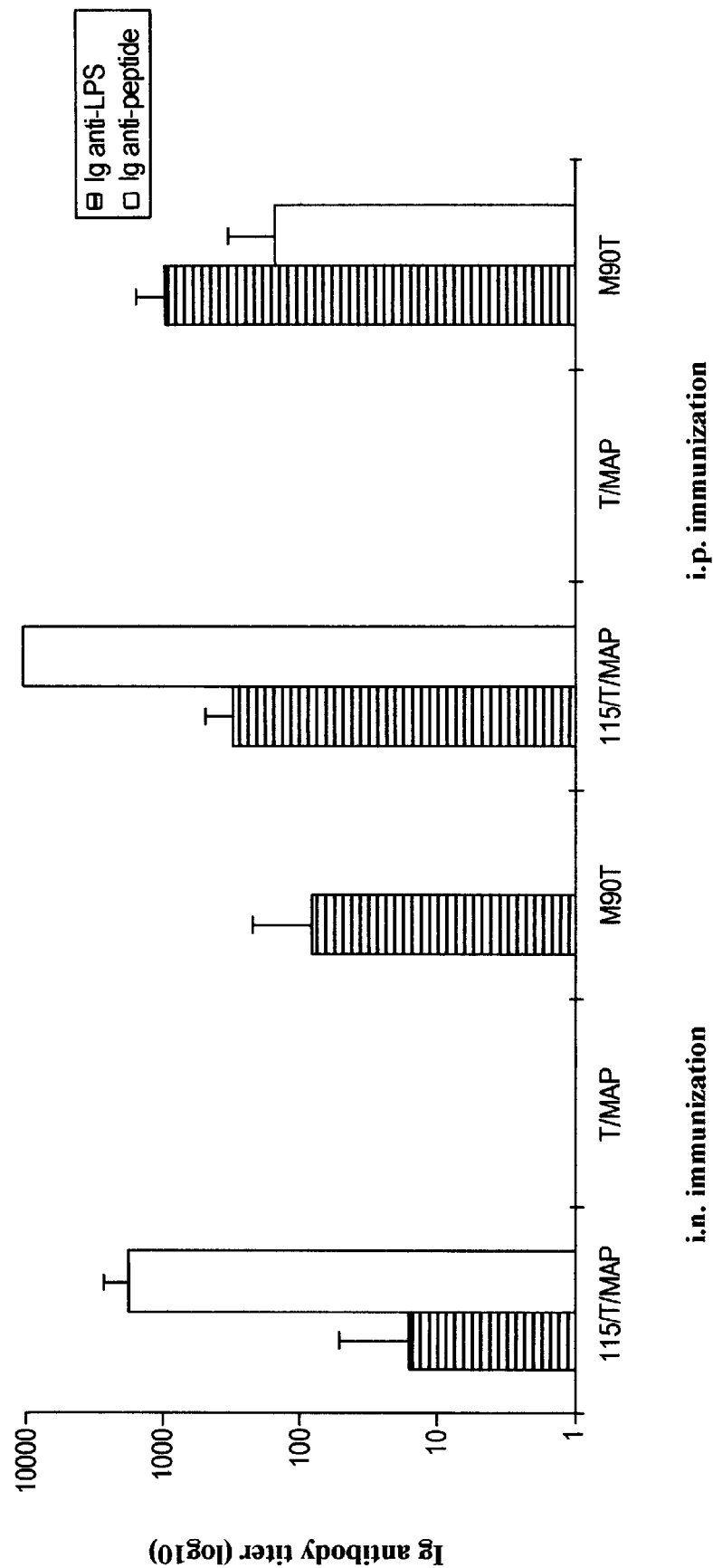

FIG. 6 shows the anti-LPS and anti-peptide Ig responses in mice following immunizations with Multi-branched Associated Peptides (MAPs). Three groups of 5 mice were immunized with either 115/T/MAP, T/MAP, or M90T (S. flexneri 5a strain) either intraperitoneally (i.p.) or intranasally (i.n.). Serum anti-LPS and anti-peptide antibody titers were measured by ELISA using as antigens purified LPS of S. flexneri serotype 5a and 115/KHL, respectively. The antibody titer corresponds to the last dilution of serum given a OD twice that of the control (preimmune serum).

Figure 7:
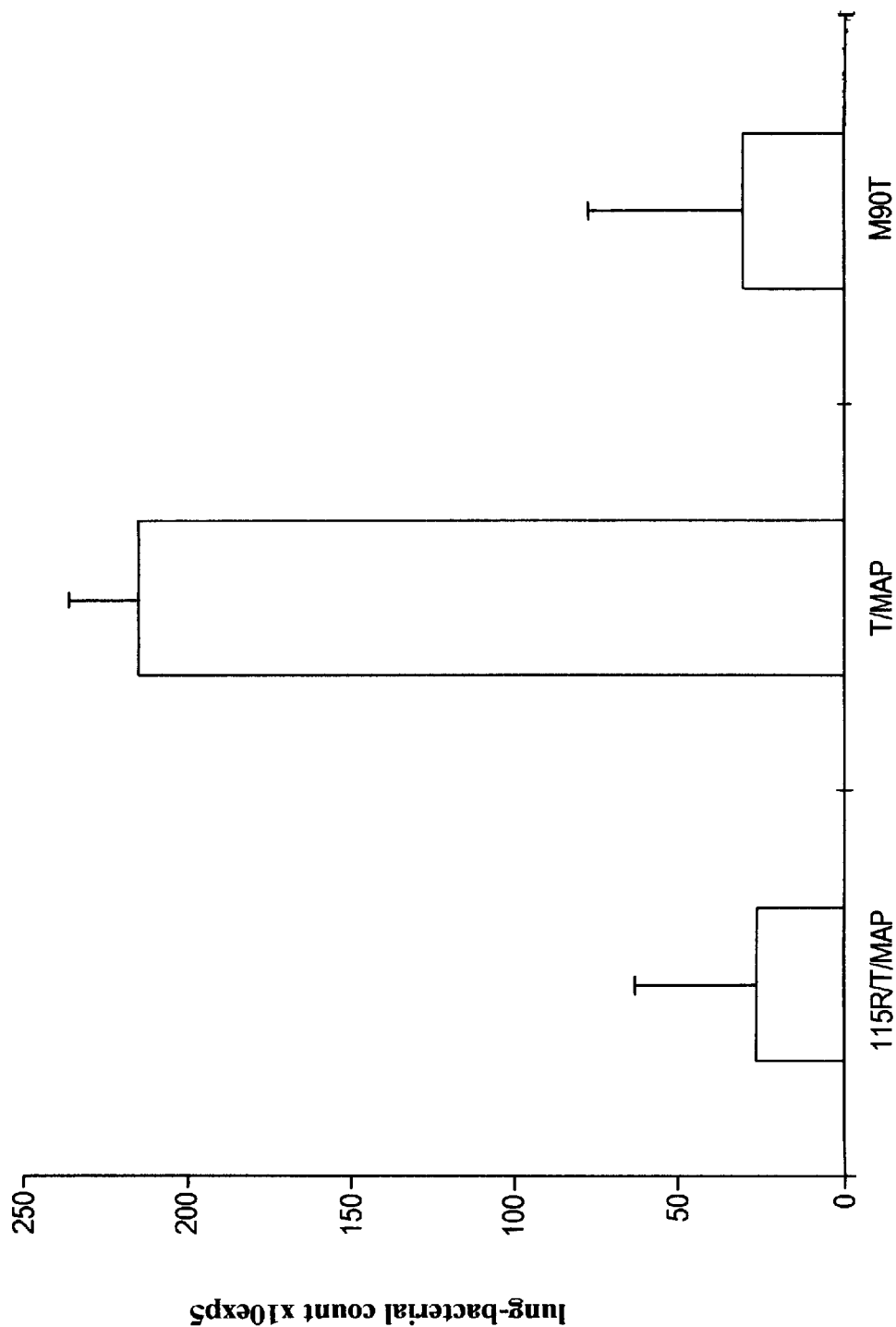

FIG. 7 shows the lung-bacterial load of mice, previously immunized i.p. with MAPs, in response to a challenge with S. flexneri serotype 5a bacteria. Mice immunized i.p. with 115/T/MAP, T/MAP, or M90T were challenged i.n. with S. flexneri serotype 5a at 15 days following the last immunization. Lung-bacterial counts were performed at 6 hours post-infection.

Figure 8:
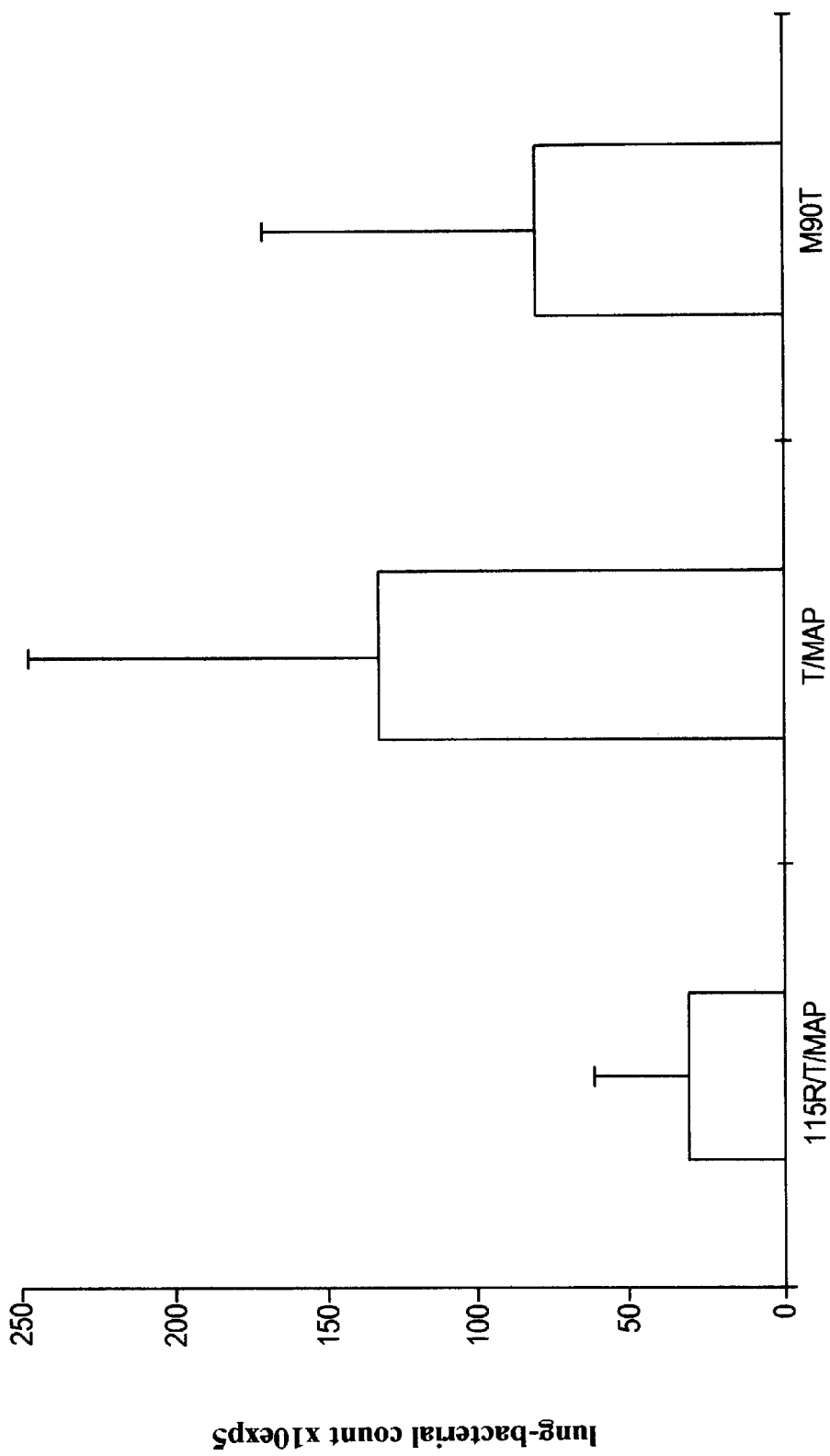

FIG. 8 shows the lung-bacterial load of mice, previously immunized i.n. with MAPs, in response to a challenge with S. flexneri serotype 5a bacteria. Mice immunized i.n. with 115/T/MAP, T/MAP, or M90T were challenged i.n. with S. flexneri serotype 5a at 15 days following the last immunization. Lung-bacterial counts were performed at 6 hours post-infection.

DETAILED DESCRIPTION OF PREFERRED EMBODIMENTS

By describing a method in order to efficiently select specific peptides from a random peptide library that mimic polysaccharide antigenic determinants as valuable immunogenic compounds inducing a protective immune response in a host against a pathogenic microorganism, this invention allows one skilled in the art to design the immunogenic polypeptides.

The results presented in the specification demonstrate that peptide sequences mimicking protective carbohydrate epitopes of pathogens selected through phage-displayed peptide libraries can act as immunogenic mimics and induce an immune response, particularly a humoral response characterized by the in vivo production of protective anti-carbohydrate antibodies. This approach represents a practical alternative to the use of anti-idiotype antibodies as mimics of carbohydrate structures. It is also a much simpler way to select peptide mimics of carbohydrates, since only two tools are required: (i) a protective monoclonal antibody specific for the carbohydrate epitope to be mimicked, and (ii) phage-displayed random peptide libraries, which are now widely available.

A polysaccharide or a carbohydrate molecule according to the present invention means an ordered polymer containing monomer units and thus containing identical epitope repeats at regular intervals. The basic units of a polysaccharide are osides. Polysaccharides may be components of complex molecules, for example by combination with proteins (glycopeptides and glycoproteins) or with lipids (lipopolyosides, including lipopolysaccharide or LPS).

A pathogenic microorganism for the purpose of the present invention is a microorganism of bacterial, fungal, or viral origin that is directly responsible for or acts as a co-factor of a disease in a mammal, specifically in a human. The microorganism expresses polysaccharide determinants at its surface, either under the form of a polysaccharide matrix (for example capsular polysaccharide) or under the form of a polysaccharide grafted onto a peptide structure (for example in surface glycoproteins).

An epitope or an epitope unit for the purpose of the present invention is a portion of an antigen molecule, which is delineated by the area of interaction with antibodies that are specific to this particular antigen.

A protective antibody for the purpose of the present invention is an antibody directed to a specific polysaccharidic antigen from a pathogenic microorganism, which is able to protect a mammalian host against an infection by the pathogenic microorganism.

A monoclonal antibody having a high affinity for a surface polysaccharide antigen for the purpose of the present invention is a monoclonal antibody, wherein monoclonal antibody binding on immobilized LPS is reached with from 1 to 2 ng LPS in solution. An illustrative assay to ensure that a monoclonal antibody conforms with the above definition of a high affinity monoclonal antibody is disclosed hereinafter.

A monoclonal antibody having a high specificity for a surface polysaccharide antigen of a given pathogenic microorganism for the purpose of the present invention is an antibody, which does not exhibit significant cross-reactivity with another antigen.

A peptide or polypeptide according to the present invention is an oligomer in which the monomers are amino acids, which are joined together through amide bonds. In the context of this specification, it should be appreciated that when alpha-amino acids are used, they can be the L-optical isomer or the D-optical isomer. Other amino acids useful in the present invention include unnatural amino acids, such as beta-alanine, phenylglycine, homoarginine and the like. Other modifications of the natural amino acid composition are described elsewhere throughout the instant specification. Standard abbreviations for amino acids are used (e.g. P for proline). These abbreviations are included in Stryer, Biochemistry, Third Ed. (1988), which is incorporated herein by reference for all purposes.

An immune response according to the present invention is a humoral and/or a cellular immune response. Protection according to the present invention is intended reduction of the bacterial load in the murine model.

In the present invention, several peptides that bind with a high specificity and a high affinity to at least one monoclonal antibody directed against the O-antigen (O—Ag) of *Shigella flexneri* serotype 5a LPS have been selected from random peptide libraries for purposes of illustration. These peptides have been demonstrated to be capable of inducing a protective immune response against the pathogen.

In order to select the immunogenic polypeptide mimics, phage clones of a random phage-displayed peptide library were tested for their ability to compete with the O—Ag for binding to a specific monoclonal antibody in an ELISA assay. Nineteen peptide sequences mimicking protective carbohydrate epitopes of the O—Ag were selected by the use of phage-displayed 9-mer peptide libraries. Because of the high specificity and the high affinity of the monoclonal antibodies directed against O—Ag used in the present invention, only two rounds of screening selection are needed in order to select good peptide mimics.

In particular, it has now been shown that the two monoclonal antibodies used, respectively, mIgA C5 and mIgA I3, recognize the 5a serotype of the O—Ag from the LPS of *S. flexneri*, but do not bind at all to the 2a serotype despite the small structural differences between the O—Ag belonging to each serotype. The basic repeat unit of the O—Ag of *S. flexneri* is composed of three rhamnose residues chain-linked to a N-acetyl glucosamine. In serotype 5a, the second rhamnose residue is branched with a glucose residue, whereas in serotype 2a it is the third rhamnose residue that is branched with a glucose residue (See FIG. 1).

The binding capacities of the mIgA C5 monoclonal antibody to the lipopolysaccharide (LPS) of *S. flexneri* have been assayed. Briefly, the antibodies are incubated overnight in the presence of increasing concentrations of LPS of *S. flexneri* serotype 5a. Then the unbound antibodies are quantified by an ELISA assay using LPS of *S. flexneri* serotype 5a. It has been found that 50% inhibition of binding of the antibodies to immobilized LPS is reached for 1 to 2 ng of free LPS.

It has also been shown that the selected peptide mimics induce anti-O—Ag antibodies in mice. The antibodies are specific for the serotype 5a. These antibodies are able to recognize O—Ag molecules of molecular weight ranging from 950 (1 unit) to 16,150 (17 units).

Furthermore, it has been demonstrated that the above immunogenic polypeptide mimic-induced antibodies recognize and bind to *S. flexneri* serotype 5a, but not serotype 2a bacteria.

These results support the fact that the immunogenic polypeptide mimic-induced antibodies are able to interact with the pathogenic microorganism in an in vivo situation.

Furthermore, the antibodies raised against the immunogenic polypeptide mimics of the invention protect the host to which they are administered against an infection with the pathogenic organism expressing the polysaccharide mimicked by the polypeptide according to the invention as assayed as described hereinafter.

The hybridoma cell line producing the mIgA C5 monoclonal antibody is part of this invention and has been deposited at the CNCM (Collection Nationale de Cultures de Microorganismes) under the accession number I-1916.

The assays used to ensure that the antibodies are induced in vivo against the immunogenic polypeptide mimic of the invention are described hereinafter, more particularly in the case of a *S. flexneri* infection, but the assay is easily transposable by one skilled in the art for other bacterial, fungal, or viral infections using the teachings of the instant specification, optionally in combination with the general knowledge of prior art in this particular technical field.

Amino acid sequences of immunogenic polypeptide mimics, which have been selected for exemplification of the invention only, and which induce a protective immune response against the pathogenic microorganism *S. flexneri* serotype 5a are the following:

SEQ ID NO. 1: R1-YKPLGALTH-R2, wherein R1 and R2 each represents either a cysteine residue or a hydrogen atom. This polypeptide is expressed by the phage clone p100c; and SEQ ID NO. 2: KVPPWARTA; this polypeptide is expressed by the phage clone p115.

The above described polypeptides of specified amino acid sequences are part of the present invention.

The peptide sequences selected as mimics of protective carbohydrate epitopes of the *S. flexneri* serotype 5a O—Ag by screening the phage-displayed nonapeptide libraries comprise a varying number of aromatic amino acids, at least one per sequence.

This invention constitutes the first example of immunogenic mimicry of carbohydrate determinants by peptide sequences selected from phage-displayed peptide libraries. It should be noted that the peptide inserts of the immunogenic mimics p100c and p115 share no obvious consensus sequence with most of the other selected clones, and do not even resemble each other's sequence. Despite having been both selected using mIgA I3, they derive from two different libraries (p100c insert is Cys-flanked), and have also a different pattern of recognition with mIgA C5. More interestingly, p100c and p115 are both able to raise a specific anti-carbohydrate antibody response upon mice immunization, but p100c is not able to inhibit p115-induced antibody binding to LPS and vice versa. Protection can be achieved in mice following immunization with p115 coupled to a carrier system, such as MAP (Multi-branched Associated Peptide).

The successful strategy of this invention is of great interest for the development of a new type of anti-polysaccharide vaccine. Immunogenic peptide mimics of protective carbohydrate epitopes of the most frequent serotypes of the Shigella species responsible for either the endemic or epidemic form of shigellosis, can be combined to develop a multivalent subunit vaccine. As phage particles might prove unsuitable for vaccination, the capacity of the mimics used as peptides to elicit anti-carbohydrate antibodies are, to date, the most industrially valuable vaccinal tool.

Using the teachings of this invention, and using the techniques described herein, optionally in combination with techniques already known in the art, one of ordinary skill in the art is now in possession of the knowledge necessary to select and/or design immunogenic polypeptides that mimic carbohydrate antigenic determinants of a pathogenic microorganism where the polypeptides are able to induce a protective immune response against the pathogenic microorganism.

Thus, as it has already been mentioned, the present invention is directed to an immunogenic polypeptide, which comprises an epitope recognized by a protective monoclonal antibody having a high affinity and a high specificity for a surface polysaccharide of a pathogenic organism. The polypeptide induces an immune response in vivo against the pathogenic organism. The pathogenic microorganism concerned can be of bacterial, fungal or viral origin, providing that the pathogenic microorganism expresses at least one polysaccharide antigen that is recognized by specific protective antibodies.

The pathogenic microorganism can be of bacterial origin, such as for example Shigella, Salmonella, Pneumococci, Streptococci (e.g. *Streptococcus pneumoniae*), Staphylococci, Meningococci, pathogenic strains of *Escherichia coli, Bacteroides fragilis* or also Klebsiella (e.g. *Klebsiella pneumoniae*).

The pathogenic microorganism can be of viral origin, such as for example human immunodeficiency viruses (e.g. strains of HIV-1 or HIV-2), feline immunodeficiency virus (FIV), human rotaviruses, human paramyxoviruses (e.g. respiratory syncitial viruses, parainfluenza viruses, Sendai viruses), and influenza viruses (e.g; *Haemophilus influenza*).

The pathogenic microorganism can be of fungal origin, such as pathogenic strains of Candida (e.g. *Candida albicans*) or *Neurospora crassa*.

In a preferred embodiment of the immunogenic polypeptide according to the present invention, the epitope unit of the polypeptide has about 6 to about 50 amino acids in length, preferably about 6 to about 20 amino acids in length, and most preferably about 6 to about 15 amino acids in length, and is capable of inducing in vivo a protective immune response against a polysaccharide antigen, which is expressed by a pathogenic microorganism. An immunogenic polypeptide having a long amino acid chain (from 25 to 50 amino acids in length) is preferably used in case of conformational epitope units. Furthermore, a large epitope unit is expected to carry both a B-epitope and a T-epitope.

Also part of the immunogenic polypeptides of the present invention are those polypeptides that comprise, but are not limited to, at least one epitope unit recognized by a protective monoclonal antibody having a high affinity and a high specificity for a surface polysaccharide of a pathogenic microorganism.

The present invention also pertains to a method for selecting an immunogenic polypeptide comprising an epitope recognized by a protective monoclonal antibody having a high affinity and a high specificity for a surface polysaccharide of an infectious organism, wherein the polypeptide is capable of inducing an immune response in vivo against the infectious organism. The method comprises:

(A) selecting, among the polypeptides from a random peptide library those that exhibit the following characteristics:
  binding with a high affinity to a monoclonal antibody having a high affinity and a high specificity for a surface polysaccharide from an infectious microorganism; and
  inducing an immune response in vivo against the infectious microorganism; and
(B) identifying the polypeptide selected at step (A).

In one specific embodiment of this method, step (A) is preceded by preparing a random peptide library. The random library of polypeptides most preferably comprises a phage-displayed peptide random library.

In another specific embodiment of the method of the invention, step (A) is preceded by preparing a monoclonal antibody having a high affinity and a high specificity for the surface polysaccharide of the infectious microorganism.

The immunogenic polypeptides according to the present invention, especially the polypeptides of SEQ ID No. 1 and SEQ ID No. 2, allow the preparation of specific polyclonal or monoclonal anti-polysaccharide antibodies.

Because anti-polysaccharide antibodies are usually very difficult to obtain in a significant quantity and with good specificity and affinity properties when using the polysaccharide molecule itself as the antigen, it is another object of the present invention to provide for specific anti-polysaccharide antibodies obtained by immunizing an animal with an immunogenic polypeptide of the invention. These antibodies directed against the immunogenic polypeptide according to the present invention recognize specifically polysaccharide antigens expressed by a given pathogenic microorganism of bacterial, fungal, or viral origin and are thus useful as diagnostic means in order to identify the presence of the pathogenic microorganism in a biological sample, preferably a tissue or a biological fluid, such as for example an infected host's plasma or serum.

Specifically, in a preferred embodiment, the monoclonal or polyclonal antibody according to the invention recognizes the polypeptides of SEQ ID No. 1 and SEQ ID No. 2.

The antibodies can be prepared from hybridomas according to the technique described by Phalipon et al. in 1995 or also by Kohler and Milstein in 1975. The polyclonal antibodies can be prepared by immunization of a mammal, especially a mouse or a rabbit, with a polypeptide according to the invention combined with an adjuvant of immunity, and then by purifying the specific antibodies contained in the serum of the immunized animal on an affinity chromatography column on which has previously been immobilized the polypeptide that has been used as the antigen.

The present invention is also directed to a diagnostic method for detecting the presence of a pathogenic microorganism tin a biological sample. The diagnostic method comprises:

(A) bringing into contact the biological sample expected to contain a given pathogenic microorganism with a purified monoclonal or polyclonal antibody according to the invention; and
(B) detecting antigen-antibody complexes formed.

In a specific embodiment of this diagnostic method, step (A) is preceded by preparing a purified preparation of the anti-immunogenic polypeptide monoclonal or polyclonal antibody.

In a preferred embodiment of the diagnostic method of the invention, the method is an immunoassay, including enzyme linked immunoassay (ELISA), immunoblot, or radioimmunoassay (RIA). These techniques are all available from the prior art.

A typical preferred immunoassay according to the invention comprises the following:

(A) incubating microtitration plate wells with increasing dilutions of the biological sample to be assayed;
(B) introducing into the microtitration plate wells a given concentration of a monoclonal or polyclonal antibody according to the invention; and
(C) adding a labeled antibody directed against human or animal immunoglobulins, the labeling of the antibodies being, for example, an enzyme that is able to hydrolyze a substrate molecule, the substrate molecule hydrolysis inducing a change in the light absorption properties of the substrate molecule at a given wavelength, for example at 550 nm.

The present invention also concerns a diagnostic kit for the in vitro diagnosis of an infection by a pathogenic microorganism. The kit comprises the following elements:

(A) purified preparation of a monoclonal or a polyclonal antibody according to the invention;

(B) suitable reagents allowing the detection of antigen/antibody complexes formed, these reagents preferably carrying a label (a marker), or being recognized themselves by a labeled reagent; and optionally (C) a reference biological sample containing the pathogenic microorganism antigen recognized by the purified monoclonal or polyclonal antibody (positive control); and optionally (D) a reference biological sample that does not contain the pathogenic microorganism antigen recognized by the purified monoclonal or polyclonal antibody (negative control).

The present invention is also directed to a polyclonal or a monoclonal antibody directed against an immunogenic peptide according to the invention. More specifically, the polyclonal or monoclonal antibody recognizes a bacterium belonging to the Shigella species when it has been prepared using an immunogenic polypeptide of sequence SEQ ID No. 1 or SEQ ID No. 2 as the antigen.

Also part of the present invention are polypeptides that are homologous to the initially selected polypeptide bearing at least an epitope unit. By homologous peptide according to the present invention is meant a polypeptide containing one or several amino acid substitutions in the amino acid sequence of the initially selected polypeptide carrying an epitope unit. In the case of an amino acid substitution, one or several consecutive or non-consecutive amino acids are replaced by "equivalent" amino acids. The expression "equivalent" amino acid is used herein to name any amino acid that may be substituted for one of the amino acids belonging to the initial polypeptide structure without decreasing the binding properties of the corresponding peptides to the monoclonal antibody that has been used to select the parent peptide and without decreasing the immunogenic properties against the specified pathogenic microorganism.

These equivalent amino acids can be determined either by their structural homology with the initial amino acids to be replaced, by the similarity of their net charge, and by the results of the cross-immunogenicity between the parent peptides and their modified counterparts.

The peptides containing one or several "equivalent" amino acids must retain their specificity and affinity properties to the biological targets of the parent protein, as it can be assessed by a ligand binding assay or an ELISA assay. For example, amino acids can be placed in the following classes: non-polar, uncharged polar, basic, and acidic. Conservative substitutions, wherein an amino acid of one class is replaced with another amino acid of the same type, fall within the scope of the subject invention so long as the substitution does not materially alter the biological activity of the compound. Table 1 provides a listing of examples of amino acids belonging to each class.

Examples of Amino Acids In Different Classes

| Class of Amino acid | Examples of amino acids |
| --- | --- |
| Non-polar | A, V, L, I, P, M, F, W |
| Uncharged polar | G, S, T, C, Y, N, Q |
| Acidic | D, E |
| Basic | K, R, H |

By modified amino acid according to the present invention is also meant the replacement of a residue in the L-form by a residue in the D form or the replacement of a glutamic acid (E) residue by a pyroglutamic acid compound. The synthesis of peptides containing at least one residue in the D-form is, for example, described by Koch et al. in 1977.

As an illustrative example, it should be mentioned the possibility to realize substitutions without a deep change in the immunogenic polypeptide binding properties of the corresponding modified peptides by replacing, for example, leucine by valine, or isoleucine, aspartic acid by glutamic acid, glutamine by aspargine arginine by lysine etc., it being understood that the reverse substitutions are permitted in the same conditions.

In order to design peptides homologous to the immunogenic polypeptides according to the present invention, one skilled in the art can also refer to the teachings of Bowie et al. (1990).

A specific, but not limiting, embodiment of a modified peptide molecule of interest according to the present invention, which comprises a peptide molecule that is resistant to proteolysis, is a peptide in which the —CONH— peptide bond is modified and replaced by a ($CH_2NH$) reduced bond, a (NHCO) retro inverso bond, a ($CH_2$—O) methylene-oxy bond, a ($CH_2$—S) thiomethylene bond, a ($CH_2CH_2$) carba bond, a (CO—$CH_2$) cetomethylene bond, a (CHOH—$CH_2$) hydroxyethylene bond), a (N—N) bond, an E-alcene bond, or also a —CH=CH— bond.

The immunogenic polypeptides according to the present invention can be prepared in a conventional manner by peptide synthesis in liquid or solid phase by successive couplings of the different amino acid residues to be incorporated (from the N-terminal end to the C-terminal end in liquid phase, or from the C-terminal end to the N-terminal end in solid phase), wherein the N-terminal ends and the reactive side chains are previously blocked by conventional groups.

For solid phase synthesis the technique described by Merrifield can be used in particular. Alternatively, the technique described by Houbenweyl in 1974 can also be used, or generally any chemical synthesis method well known in the art, such as for example a chemical synthesis method performed with a device commercialized by Applied Biosystems.

In order to produce a peptide chain using the Merrifield process, a highly porous resin polymer can be used on which the first C-terminal amino acid of the chain is fixed. This amino acid is fixed to the resin by means of its carboxyl groups and its amine function is protected, for example, by a t-butyloxycarbonyl group.

The peptides or pseudopeptides according to the present invention are advantageously combined with or contained in a heterologous structure, or polymerized in such a manner as to enhance their ability to induce a protective immune response against the pathogenic microorganism. As a particular embodiment of the immunogenic polypeptide according to the present invention, the immunogenic polypeptide can comprise more than one epitope unit, preferably about 2 to about 20 epitope units, more preferably about 2 to about 15 epitope units, and most preferably about 3 to about 8 epitope units per polypeptide molecule, usable as an active principle of a vaccine composition.

The immunogenic polypeptides of the invention that comprise more than one epitope unit are herein termed "oligomeric polypeptides". The polymers can be obtained by the technique of Merrifield or any other conventional peptide polymer synthesis method well known in the art.

The peptides thus obtained can be purified, for example by high performance liquid chromatography (HPLC), such as reverse phase and/or cationic exchange HPLC, as described by Rougeot et al. in 1994.

As another particular embodiment of the oligomeric immunogenic polypeptides according to the present invention, the peptides or pseudopeptides are embedded within a peptidic synthetic matrix in order to form a MAP (Multi-branched Associated Peptide) type structure. Such MAP structures as well as their method of preparation are described by Tam in 1988 or in the PCT patent application No. WO 94/28915 (Hovanessian et al.). The embedding of the peptides or pseudopeptides of therapeutic value according to the present invention within MAP type structures can cause an increase in the immunogenic and/or protective properties of the initial molecules as regards to the pathogenic microorganism infection.

In order to improve the antigenic presentation of the immunogenic polypeptides according to the present invention to the immune system, the immunogenicity of the selected polypeptide mimics when presented via a MAP (Multiple Antigen Peptide) construct has been studied. This kind of presentation system is able to present more than one copy of a selected epitope unit per molecule (4 to 8 immunogenic polypeptide mimics per MAP construct molecule) embedded in a non-immunogenic "carrier" molecule.

The inventors have synthesized MAP constructs by the Merrifield solid-phase method (Merrifield et al., 1963) that comprise a lysine core on which have been grafted four peptide chains of either sequence SEQ ID No. 1 (MAP-p100c) or SEQ ID No 2 (MAP-p115). Mice were injected repeatedly with 50 mg to 100 mg of the antigen in PBS, Serum as well as local anti-LPS IgG, and IgA antibody titers have been determined by ELISA using purified *S. flexneri* serotype 5a LPS as antigen.

MAP-p115 is recognized by both IgA C5 and IgA I3 monoclonal antibodies that have been used for selecting the p100c and p115 peptide mimics. MAP-p115 is also recognized by the serum antibodies of mice immunized with the recombinant phages expressing the p115 polypeptide. Thus, the anti-peptide antibodies raised after immunization with p115 phage clones are able to recognize the selected peptide of sequence SEQ ID No. 2 outside the phage environment when the antigen is presented to the cells via a MAP construct.

Thus, another object of the present invention comprises peptide constructs that are able to ensure an optimal Representation to the immune system of the carbohydrate peptide mimics according to the invention.

In a specific embodiment of the peptide constructs according to the invention, the peptide mimics (the epitope units) are part of a MAP construct as defined above, such MAP construct comprising from four to eight epitope units per molecule, for example grafted on a lysine core as described hereinafter.

Generally, an immunogenic polypeptide according to the present invention will comprise an additional T-epitope that is covalently or non-covalently combined with said polypeptide of the invention. In a preferred embodiment, the additional T-epitope is covalently linked to the immunogenic polypeptide.

Illustrative embodiments of a suitable T-cell epitope to be combined with an immunogenic peptide mimic according to the invention are, for example, the following:

hepatitis delta T-cell epitopes (Nisini et al., 1997);

a T-cell epitope from the Influenza virus (Fitzmaurice et al., 1996);

a T-cell epitope of woodchuck hepatitis virus (Menne et al., 1997);

a T-cell epitope from the rotavirus VP6 protein (Banos et al., 1997);

a T-cell epitope from the structural proteins of entroviruses, specifically from the VP2, VP3, and VP1 capsid proteins (Cello et al., 1996);

a T-cell epitope from tetanus toxin (Astori and Kraehenbuhl, Molecular Immunology 1996, Vol. 33, pp. 1017–1024);

a T-cell epitope from Streptococcus mutans (Senpuku et al., 1996); and a T-cell epitope from the VP1 capsid protein of the foot and mouth disease virus (Zamorano et al., 1995).

Preferred additional T-cell epitopes used according to the present invention are, for example, universal T-cell epitopes, such as tetanus toxoid or also the VP1 poliovirus capsid protein (Graham et al., 1993). In a most preferred embodiment, the T-cell epitope comprises a peptide comprised between the amino acid in position 103 and the amino acid in position 115 of the VP1 poliovirus capsid protein.

Thus, the MAP construct may comprise an additional T epitope, which is covalently linked to the immunogenic polypeptide of the MAP, the orientation being chosen depending on the immunogenic polypeptide to be used to prepare the MAP construct. Accordingly, the additional T-epitope can be located at the external end (opposite to the core) of the MAP, or conversely the additional T-epitope can be directly linked to the core of the MAP construct, thus preceding the immunogenic polypeptide, which is then external to the MAP construct.

In another embodiment of the peptide constructs according to the present invention, the immunogenic polypeptide is directly coupled with a carrier molecule, such as KLH (Keyhole Limpet Hemocyanin) or preferably with tetanus toxoid.

The immunogenic polypeptides according to the invention can be presented in different ways to the immune system. In one specific embodiment the immunogenic carbohydrate peptide mimics of the invention can be presented under the form of ISCOMs (Immunostimulating complexes) that are composed of Quil A (a saponin extract from *Quilaja saponaria* olina bark), cholesterol and phospholpids associated with the immunogenic polypeptide (Mowat et al., 1991; Morein, 1990, Kersten et al., 1995).

The immunogenic polypeptides of the invention can also be presented in the form of biodegradable microparticles (microcapsules or microspheres), such as, for example, lactic and glutamic acid polymers as described by Aguado et al. in 1992, also termed poly(lactide-co-glycolide) microcapsules or microspheres.

Other microparticles used to present the polypeptide mimics of the invention are synthetic polymer microparticles carrying on their surface one or more polypeptide mimics covalently bonded to the material of the microparticles, said peptide mimic(s) each carrying one or more epitope units and being present at a density of between $10^4$ and $5 \times 10^5$ molecules/$\mu m^2$. These microparticles have an average diameter of about 0.25 $\mu$m to about 1.5 $\mu$m, and preferentially of about 1 $\mu$m so as to be able to be presented to CD4+T lymphocytes by phagocytic cells. These microparticles are more particularly characterized in that the covalent bond is formed by reaction between the $NH_2$ and/or CO groups of the immunogenic peptide mimic and the material making up the microparticle. Advantageously, such a bond is created by a bridging reagent as intermediate, such as glutaraldehyde or carbodiimide. The material of the microparticle can advantageously be a biocompatible polymer, such as an acrylic polymer, for example polyacrolein or polystyrene, or the poly(alpha-hydroxy acids), copolymers of lactic and glycolide acids or lactic acid polymers, wherein the polymers are homopolymers or hetero- or copolymers. The above-described microparticles are described in French Patent Application No. FR 92 10879, filed on Sep. 11, 1992 (Leclerc et al).

The immunogenic polypeptide mimics of the invention can also be included within or adsorbed onto liposome particles, such as those described in PCT Patent Application No. PCT/FR95/00215 published on Aug. 31, 1995 (Riveau et al.).

The present invention is also directed to an immunogenic composition comprising an immunogenic polypeptide according to the invention, notably in the form of a MAP construct or a peptide construct as defined above, and including the oligomeric immunogenic polypeptides described hereinbefore, or also in a microparticle preparation.

The invention also pertains to a vaccine composition for immunizing humans and other mammals against a fungal, bacterial, or viral infection, comprising an immunogenic composition as described above in combination with a pharmaceutically compatible excipient (such as saline buffer), optionally in combination with at least one adjuvant of immunity, such as aluminum hydroxide or a compound belonging to the muramyl peptide family. Various methods for achieving adjuvant effect for the vaccine include the use of agents such as aluminum hydroxide or phosphate (alum), commonly used as 0.05 to 0.1 percent solution in phosphate buffered saline, in admixture with synthetic polymers of sugars (Carbopol) used as 0.25% solution. Another suitable adjuvant compound is DDA (dimethyldioctadecylammonium bromide), as well as immune modulating substances, such as lymphokines (e.g. gamma-IFN, IL-1, IL-2 and IL-12) and also gamma-IFN inducer compounds, such as poly I:C.

Preparation of vaccines, which contain polypeptides as active ingredients, is generally well understood in the art as exemplified by U.S. Pat. Nos. 4,608,251; 4,601,903; 4,599,231; 4,599,230, 4,596,792, and 4,578,770, all incorporated herein by reference.

The vaccine according to the present invention is advantageously prepared as an injectable composition either as a liquid solution or suspension. The vaccine can also be provided in solid form suitable for solution in or suspension in a liquid prior to injection.

The active immunogenic polypeptide contained in the vaccinal composition is generally mixed with excipients, which are pharmaceutically acceptable and compatible, such as for example, water, saline, dextrose, glycerol, ethanol, or a combination of more than one of the above excipients. In addition, if desired, the vaccine composition can contain minor amounts of auxiliary substances, such as wetting or emulsifying agents, pH buffering agents, or adjuvants that enhance the effectiveness of the vaccines.

The vaccines are conventionally administered parenterally, by injection, for example, either subcutaneously or intramuscularly. Additional formulations are suitable for other modes of administration, including suppositories, and in some cases oral formulations, which may be preferred embodiments for the development of a desired mucosal immunity. For suppositories, traditional binders and carriers include, for example, polyalkalene glycols or triglycerides. Suppositories can be formed from mixtures containing the active immunogenic polypeptide of the invention in the range of about 0.5% to about 10%, preferably about 1 to about 2% by weight. Oral formulations include such normally employed excipients as, for example, pharmaceutical grades of mannitol, lactose starch, magnesium stearate, sodium saccharine, cellulose, or magnesium carbonate. These compositions take the form of solutions, suspensions, tablets, pills, capsules, sustained release formulations, or powders, and contain about 10 to about 95% by weight of the active immunogenic polypeptide of the invention, preferably about 25 to about 70% by weight.

The immunogenic polypeptide of the invention can be formulated into the vaccine in neutral or salt form. Pharmaceutically acceptable salts include acid addition salts (formed with free amino groups of the peptide), and which are formed with inorganic acids such as, for example, hydrochloric or phosphoric acids, or such organic acids as acetic, oxalic, tartaric, or mandelic acid. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, or procaine.

The vaccine compositions of the invention are administered in a manner compatible with the dosage formulation and in such amount as will be therapeutically effective and immunogenic. The quantity to be administered depends on the subject to be treated, including, e.g., the capacity of the individual's immune system to mount an immune response. Suitable dosage ranges are of the order of several hundred micrograms active immunogenic polypeptide with a preferred range about 0.1 $\mu$g to about 1000 $\mu$g, preferably about 1 $\mu$g to about 300 $\mu$g, and especially about 10 $\mu$g to about 50 $\mu$g. The dosage of the vaccine will depend on the route of administration and will vary according to the age of the patient to be vaccinated and, to a lesser degree, the size of the person to be vaccinated.

Preferably, both in the case of an immunogenic polypeptide carrying a single epitope unit and in the case of an immunogenic polypeptide carrying several epitope units, the vaccine composition is administered to human in an amount of about 0.1 to about 1 $\mu$g immunogenic polypeptide per kilogram patient's body weight, preferably about 0.5 $\mu$g/kg of body weight, this representing a single vaccinal dose for a given administration. In the case of patients affected with immunological disorders, such as for example immunodepressed patients, each injected dose preferably contains half the weight quantity of the immunogenic polypeptide contained in a dose for a healthy patient.

In many instances, it will be necessary to proceed with multiple administrations of the vaccine composition according to the present invention, usually not exceeding six administrations, more preferably not exceeding four vaccinations, and preferably one or more, usually at least about three administrations. The administrations will normally be at from two to twelve week intervals, more usually from three to five week intervals. Periodic boosters at intervals of 1–5 years, usually three years, will be desirable to maintain the desired levels of protective immunity.

Preferably, the vaccine composition is administered several times. As an illustrative example, three vaccinal doses as defined hereinabove are administered to the patient at time t0, at time t0+1 month, and at time t0+12 months. Alternatively, three vaccinal doses are administered at time t0, at time t0+1 month, and at time t0+6 months.

The course of the immunization can be followed by in vitro proliferation assays of PBL (peripheral blood lymphocytes) co-cultured with the immunogenic polypeptide of the invention, and especially by measuring the levels of gamma-IFN released from primed lymphocytes. The assays can be performed using conventional labels, such as radionuclides, enzymes, or fluorescent compounds. These techniques are well known in the art and found notably in the U.S. Pat. Nos. 3,731,932, 4,174,384, and 3,949,064, which are incorporated by reference herein.

As described above, a measurement of the effect of the polypeptides in the vaccine compositions according to the present invention can be to assess the gamma-IFN released from memory T-lymphocytes. The stronger the immune response, the more gamma-IFN will be released. Accordingly, a vaccine composition according to the invention comprises a polypeptide capable of releasing from memory T-lymphocytes at least about 1500 pg/ml, such as about 2000 pg/ml, preferably about 3000 pg/ml gamma-IFN, in the above-described in vitro assays.

In mice that are administered a dose comparable to the dose used in a human, antibody production is assayed after recovering immune serum and revealing immune complex formed between antibodies present in the serum samples and the immunogenic polypeptide contained in the vaccine composition, using the usual methods well known in the art.

The immunogenic polypeptides used in the vaccinal strategy according to the present invention can also be obtained using genetic engineering methods. The one skilled in the art can refer to the known sequence of the phage insert that expresses a specific epitope unit of an immunogenic polypeptide mimic of the invention and also to the general literature to determine the appropriate codons that can be used to synthesize the desired peptide. There is no need to say that the expression of the polynucleotide that encodes the immunogenic polypeptide mimic of interest may be optimized, according to the organism in which the sequence has to be expressed and the specific codon usage of this organism (mammal, plant, bacteria, etc.). For bacteria and plant, respectively, the general codon usages can be found in European patent application No. EP 0 359 472 (Mycogen).

As an alternative embodiment, the epitope unit of the immunogenic polypeptide mimic according to the present invention is recombinantly expressed as a part of longer polypeptide that serves as a carrier molecule. Specifically, the polynucleotide coding for the immunogenic polypeptide of the invention, for example a polypeptide having an amino acid length between 10 and 200 amino acid residues, is inserted at at least one permissive site of the polynucleotide coding for the Bordetella cyaA adenylate cyclase, for example, at a nucleotide position located between amino acids 235 and 236 of the Bordetella adenylate cyclase. Such a technique is fully described in the U.S. Pat. No. 5,503,829 granted on Apr. 2, 1996 (Leclerc et al.).

In another embodiment of the vaccine composition according to the present invention, the nucleotide sequence coding for the desired immunogenic polypeptide carrying one or more epitope units is inserted in the nucleotide sequence coding for surface protein of *Haemophilus influenza*, such as described in PCT Application No. PCT/US96/17698 (The Research Foundation of State University of New York), which is incorporated by reference herein.

In another embodiment of the vaccine composition according to the invention, the composition comprises a polynucleotide coding for the immunogenic polypeptide or oligomeric peptide of pharmaceutical interest.

For the purpose of the present invention, a specific embodiment of a vaccinal strategy comprises the in vivo production of an immunogenic polypeptide, for example in an oligomeric form by the introduction of the genetic information in the mammal organism, specifically in the patient organism. This genetic information can be introduced in vitro in a cell that has been previously extracted from the organism, the modified cell being subsequently reintroduced in the said organism directly in vivo into the appropriate tissue. The method for delivering the corresponding protein or peptide to the interior of a cell of a vertebrate in vivo comprises the step of introducing a preparation comprising a pharmaceutically acceptable injectable carrier and a polynucleotide operatively coding for the polypeptide into the interstitial space of a tissue comprising the cell, whereby the polynucleotide is taken up into the interior of the cell and has a pharmaceutical effect.

In a specific embodiment, the invention provides a vaccine composition comprising a polynucleotide operatively coding for the immunogenic polypeptide of interest or one of its above-described oligomeric peptides in solution in a physiologically acceptable injectable carrier and suitable for introduction interstitially into a tissue to cause cells of the tissue to express the said protein or polypeptide.

The polynucleotide operatively coding for the immunogenic polypeptide mimic or oligomeric peptide can be a vector comprising the genomic DNA or the complementary DNA (cDNA) coding for the corresponding protein or its protein derivative and a promoter sequence allowing the expression of the genomic DNA or the complementary DNA in the desired eukaryotic cells, such as vertebrate cells, specifically mammalian cells. The vector component of a therapeutic composition according to the present invention is advantageously a plasmid, a part of which is of viral or bacterial origin, which carries a viral or a bacterial origin of replication and a gene allowing its selection, such as an antibiotic resistance gene. By "vector" according to this specific embodiment of the invention is intended a circular or linear DNA molecule. This vector can also contain an origin of replication that allows it to replicate in the eukaryotic host cell, such as an origin of replication from a bovine papillomavirus.

Therapeutic compositions comprising a polynucleotide are described in PCT application No. WO 90/11092 (Vical Inc.), and also in PCT application No. WO 95/11307 (Institut Pasteur, INSERM, Université d'Ottawa), as well as in the articles of Tacson et al. (1996, Nature Medicine, 2(8):888–892) and of Huygen et al. (1996, Nature Medicine, 2(8):893–898).

In another embodiment, the DNA to be introduced is complexed with DEAE-dextran (Pagano et al., 1967, J. Virol., 1:891) or with nuclear proteins (Kaneda et al., 1989, Science, 243:375), with lipids (Felgner et al., 1987, Proc. Natl. Acad. Sci., 84:7413), or encapsulated within liposomes (Fraley et al., 1980, J. Biol. Chem., 255:10431).

In another embodiment, the therapeutic polynucleotide can be included in a transfection system comprising polypeptides that promote its penetration within the host cells as described in PCT application No. WO 95/10534 (Seikagaku Corporation).

The therapeutic polynucleotide and vector according to the present invention can advantageously be administered in the form of a gel that facilitates transfection into the cells. Such a gel composition can be a complex of poly-L-lysine and lactose as described by Midoux (1993, Nucleic Acids Research, 21:871–878) or also poloxamer 407 as described by Pastore (1994, Circulation, 90:I-517). The therapeutic polynucleotide and vector according to the invention can also be suspended in a buffer solution or be associated with liposomes.

Thus, the vaccinal polynucleotide and vector according to the invention are used to make pharmaceutical compositions for delivering the DNA (genomic DNA or cDNA) coding for the immunogenic polypeptide mimic of the invention at the site of the injection. The amount of the vector to be injected varies according to the site of injection. As an indicative dose, the vector can be injected in an amount of about 0.1 and about 100 µg of the vector in a patient.

In another embodiment of the therapeutic polynucleotide according to the invention, the polynucleotide can be introduced in vitro into a host cell, preferably in a host cell previously harvested from the patient to be treated, and more preferably a somatic cell such as a muscle cell. In a subsequent step, the cell that has been transformed with the vaccinal nucleotide coding for the immunogenic polypeptide of the invention is implanted back into the patient in order to deliver the recombinant protein within the body either locally or systemically.

Consequently, the present invention also concerns an immunogenic composition comprising a polynucleotide or an expression vector as described hereinabove in combination with a pharmaceutically acceptable vehicle allowing its administration to the human or other animal. A further embodiment of the invention comprises a vaccine composition comprising a polynucleotide or a vector as described above in combination with a pharmaceutically acceptable vehicle allowing its administration to the human or the animal.

This invention will be described in greater detail in the following Examples.

EXAMPLE 1

A. Phage-displayed Peptide Libraries and Selection of Peptide Mimics by Biopanning The two phage peptide libraries used in this study, pVIII-9aa (Felici et al., 1991) and pVIII-9aa.Cys (Luzzago et al., 1991), contain 9 amino acid random peptide inserts in the N-terminal region of the phage major coat protein (pVIII); in the latter, pVIII-9aa.Cys, the random inserts are flanked by two cysteine residues and hence can be cyclically constrained. Specific phage clones were isolated from the libraries by two rounds of affinity selection according to previously described biopanning procedures (Felici et al., 1991; Parmley et al., 1988).

In the first round, the mAb (at 1 $\mu$M concentration) was incubated overnight at +4° C. with $10^{10}$ Amp$^R$ TU of library in a total volume of 10 $\mu$l. The mixture was incubated with 0.25 $\mu$g of a biotin-conjugated goat anti-mouse IgA secondary antibody (alpha-chain specific, SIGMA, St. Louis, Mo.), which was previously pre-adsorbed overnight at +4° C. with $2\times10^{11}$ phage particles of UV-killed M13K07 in order to prevent non-specific binding, and then the phage-mAb-secondary Ab complexes were tethered on streptavidin coated dishes. The second round of affinity selection was carried out in the same way, but using 10 nM or 0.1 nM concentrations of mAb (and proportionally lower amounts of the secondary antibody). Positive phage clones were identified through plaque immunoscreening (Luzzago et al., 1993; Felici et al., 1996), and further characterized through ELISA (Smith et al., 1993; Dente et al., 1994).

B. Immunization of Mice

Six-week-old BALB/c female mice (Janvier, France) were immunized i.p. six times at 15 day intervals for the first three injections, and at 30 day intervals for the last three injections, using $10^{12}$ phage particles per immunization, purified through CsCl gradient (Smith et al., 1993). A group of ten mice was used for each of the phage clones used as immunogen. Preimmune sera were individually recovered from every mouse and used as a negative control when testing the presence of anti-S. flexneri LPS antibodies in each of the corresponding immune sera. For each of the clones inducing a positive response, another group of 10 mice was also immunized i.p. to test the reproducibility of anti-carbohydrate antibody induction. I.v. immunizations were also assessed.

C. Immunoblotting of LPS

Briefly, 2 $\mu$g per well of purified LPS diluted in Laemmli sample buffer were run into a sodium dodecyl sulfate-15% polyacrylamide gel (SDS-PAGE) (Laemmli, 1970) in the presence of urea at a concentration of 4M. After transfer to nitrocellulose, the anti-S. flexneri LPS antibodies in the serum of mice immunized with each of the different phage clones were revealed using horseradish peroxidase-labeled goat anti-mouse IgG as secondary antibody (dilution at use 1:5000; Sigma Chemical Co., St Louis, Mo.), and visualized by enhanced chemiluminescence (Amersham International, Buckinghamshire, England).

D. ELISA

ELISA was performed as previously described (Meloen et al., 1980). Briefly either 1 $\mu$g of S. flexneri LPS purified according to Westphal et al. (Westphal et al., 1965) or $10^{10}$ p100c or p115 phage particles were coated per well. Binding of specific antibodies was revealed using alkaline phosphatase-conjugated goat anti-mouse IgG as secondary antibody (dilution at use 1:5000; Biosys, Compigne, France). Antibody titers were defined as the last dilution of serum specimens leading to an OD twice that of the negative control (i.e. preimmune sera), except for the measurement of the anti-LPS titer in which incubation of sera of mice immunized with pwt (cross-reacting with the Shigella LPS core moiety) was used as the negative control. Specific inhibition of recognition of O—Ag by p100c- or p115-induced antibodies was performed in the same conditions, except that various concentrations of p100c and p115 phage particles were incubated with the p100c- and p115-immune sera before adding the sample to the well.

E. Labeling of Bacteria

Freshly grown bacteria were centrifuged onto cover-slips (700×g for 10 min) and fixed with 3.7% paraformaldehyde in phosphate-buffered saline for 20 min at room temperature. Labeling was performed, as previously described (Mounier et al., 1997), with immune sera of mice immunized with either p100c, p115, or pwt phage particles (dilution at use: 1:20). Goat anti-mouse rhodamine-conjugated immunoglobulin G (Sigma Chemical Co., St. Louis, Mo.) was used as a secondary antibody (dilution at use: 1:200). The labeled preparations were observed using a conventional fluorescence microscope (BH2-RFCA, Olympus Optical, Co, Ltd).

F. Synthesis of M Constructs

Peptides and MAP peptides were synthesized by the Merrifield solid-phase method (1) using Fmoc chemistry on a Pioneer Perseptive Biosystems synthesizer. Stepwise elongation of the peptide chains was done using HATU activation (4 eq.).

Peptides 115-Cys and 100c-Cys were synthesized on a Fmoc Cys(Trt)-PAC-PEG-PS resin (Perseptive Biosystems). After elongation of the peptide chain, the peptides were cleaved from the resin by TFA/H$_2$O/EDT/TIS (92.5/2.5/2.5/2.5) mixture for 2 hours. The resins were eliminated by filtration and the peptides recovered by precipitation in cold diethyl ether. Peptides were then purified by reverse phase HPLC on a Nucleosil 5 C18 300 □ semi-preparative column (250 mm×10 mm) using; respectively; a 15–40 and 15–30 linear gradient of acetonitrile in 0.1% aqueous TFA over 20 min at a 6 ml/min flow rate. Final purities of the two peptides were checked on a Nucleosil 5 C18 300 □ analytical column (150 mm×4.6 mm) using a 17–30 linear gradient over 20 min at a 1 ml/min flow rate using the same eluents as above.

The lysine core, (Lys)2-Lys-Ser-Ser-Lys-bAla-$NH_2$, of the MAP was synthesized on a PAL-PEG-PS resin (Perseptive Biosystems), and the tetrameric structure was obtained by incorporating two levels of Fmoc Lys(Fmoc)OH.

MAP peptides (MAP115 and MAP100C) were obtained by stepwise elongation of the peptide chain on the four amino groups of the lysine core.

After TFA/$H_2$O/TIS (95/2.5/2.5) cleavage and ether precipitation, MAP115 and MAP100C were purified by reverse phase HPLC on a Nucleosil 5 C18 300 □ semi-preparative column (250 mm×10 mm) using, respectively, a 20–40 and 15–45 linear gradient of acetonitrile in 0.1% aqueous TFA over 20 min at a 6 ml/min flow rate. Final purity of the two MAP were checked on a Nucleosil 5 C18 300 □ analytical column (150 mm×4.6 mm) using, respectively, a 20–40 and 20–50 linear gradient over 20 min at a 1 ml/min flow rate using the same eluents as above.

Positive ion electrospray mass spectrometry confirmed the purity and the molecular weight of the MAP peptides and peptides.

| Product | HPLC (anal) retention time (min) | Purity (HPLC) | Yield (mg) | MW (expected) | MW (found by ES+) |
|---|---|---|---|---|---|
| MAP115 | 15.66 | 98% | 9 | 4463.4 | 4463.3 |
| MAP100C | 12.81 | 99% | 9. | 4699.7 | 4700.0 |
| 115-Cys | 13.03 | 98% | 22 | 1042.3 | 1042.4 |
| 100C-Cys | 11.01 | 92% | 10 | 1101.6 | 1101.5 |

Abbreviations:
MAP: Multiple Antigens Peptides,
HATU: (O-(7-azabenzotriazol-1-yl)-1,1,3,3-tetramethyluronium hexafluorophosphate,
TFA: trifluoracetic acid,
EDT: ethanedithiol,
TIS: triisopropylsilane,
HPLC: high performance liquid chromatography.

G. Immunization Procedures with the Peptide Mimics

Inbred seven week-old female BALB/c mice were injected with 50 µg to 100 µg of the antigen in PBS, three times at 3-week intervals. Intraperitoneal immunizations were performed to elicit a systemic immune response, whereas intranasal immunizations were performed to elicit a local response. Samples (serum or bronchoalveolar lavages) were recovered 2 weeks after the last boost. Serum and local anti-LPS IgG and IgA antibody titers were determined by ELISA using purified LPS as antigen.

H. In vivo Protection Assays Using a Selected Immunogenic Peptide Mimic

Mice previously immunized via the systemic or intranasal routes (as described in Section H) were challenged by intranasal administration of S. flexneri virulent bacteria ($10^8$ bacteria in 20 µl). A group of non-immunized mice was used as a control. Protection was assessed by numbering the bacteria in the lungs, measurement of the level of IL-6, and histological studies as described in Phalipon et al. (1995).

I. In vivo Protection Assays with the High Affinity Anti-Polysaccharide Monoclonal Antibody
(A) Back Pack Tumor Model The back pack tumor model is performed as described by Winner et al. (1991). mIgA serum levels are measured by ELISA in mice developing a tumor. These mice are then intranasally challenged with 20 µl of a S. flexneri 5a or S. flexneri 2a culture at $5 \times 10^8$/ml. This inoculum is tenfold less (sub-lethal dose is used here) than the inoculum required for the $LD_{50}$ in this model. For each experiment, naive BALB/c mice are concomitantly challenged with the same inoculum. One day after the challenge, mice are tail bled, and serum IL-6 levels are measured following the technique described by Van Snick et al. (1986). Representative mice are killed, and their lungs are removed from the thoracic cavity after being filled with paraformaldehyde for histopathological analysis.

(B) Intranasal Administration of mIgA.

For intranasal administration of mIgA, mice are inoculated with different amounts of the purified antibody in a volume of 20 µl 1 h before being challenged as described above. At 6 h after infection, serum IL-6 levels are measured, specimens are taken for histopathological analysis, and bacterial counts in lung tissues are performed. For the latter experiments, mice are killed by cervical dislocation, and lungs are dissected and placed in 10 ml of ice-cold 0.9% NaCl, and then ground with an Ultra-turrax apparatus (Janke and Kunkel, GmbH and Co., Staufen, Germany). Serial dilutions of the resulting solution are placed on Congo red agar and incubated overnight at 37° C. For each experiment corresponding to a given amount of antibody administered intranasally, a control group of naive mice is concomitantly challenged.

For the back pack tumor model or the intranasally administered purified mIgA experiments, each experiment is comprised of 10 mice per group and is repeated three times.

J. Assay for Determining the High Affinity of the Anti-polysaccharide Monoclonal Antibodies In a first step, LPS is coated on the surface of wells of microtitration plates by an overnight incubation of 1 µg LPS per well in solution in a carbonate buffer, pH 6.0 at 4° C.

In parallel, glass tubes are filled with 125 µl of a solution containing the monoclonal antibody to be assayed at a constant concentration (for example at about 7 µg/ml). Then, increasing concentrations of a LPS solution are added to each glass tube in a final volume of 250 µl (from 0.1 µg/ml to 1 µg/ml LPS in solution) and incubated overnight at 4° C. Control tubes are included in the assay, respectively containing LPS alone or the monoclonal antibody alone.

In a second step, 100 µl of the solution contained in each above-described glass tubes is dispensed in the wells of the above-described microtitration plate and incubated per 30 min at 4° C. Then, two washings are performed with a PBS/Tween buffer (conventional ELISA assay), and the bound monoclonal antibody is conventionally revealed, for example with a peroxidase- or phosphatase-labeled anti-Ig antibody.

The LPS concentration for which 50% inhibition of binding of the assayed anti-polysaccharide monoclonal antibody is achieved is then determined.

K. Selection and Features of Phage-displayed Peptides Mimicking Protective Carbohydrate Epitopes of the S. flexneri Serotype 5a O—Ag Both mIgA C5 and mIgA I3 specific for the O—Ag of the S. flexneri serotype 5a LPS (previously shown to be protective in vivo against Shigella infection, Phalipon et al., 1995; A. Phalipon, unpublished results), were used to screen phage-displayed nonapeptide libraries, and clones interacting with these antibodies were isolated as described above.

Six different clones were selected with mIgA I3 and thirteen with mIgA C5. Five of the clones selected with mIgA I3 were shown in ELISA to interact also with mIgA C5.

Then, to select relevant peptide mimics of the carbohydrate epitopes, the phage clones were tested for their ability to compete with the antigen for binding to the antibody. Binding in of each mIgA to the selected phage clones was measured by ELISA in the presence of various concentrations of the S. flexneri serotype 5a LPS. The binding of all the phage clones to the antibody(ies) they interacted with was shown to be inhibited by LPS. The peptide sequences of the inserts of the phage clones mimicking carbohydrate determinants are summarized in Table 2. In total, nineteen peptide sequences mimicking protective carbohydrate epitopes of the O—Ag were selected by the use of two different phage-displayed peptide libraries.

An interesting common feature of all the sequences was the high frequency of aromatic amino acid residues, either tyrosine (Y), proline (P), histidine (H), tryptophan (W), or phenylalanine (F), a large part (82%) of the positive insert sequences, comprised at least two aromatic residues, and more than half (55%) at least three. Clone 12 contained five aromatic amino acids out of nine.

EXAMPLE 2

Immunogenicity of the Peptide Mimics

If the peptide sequences that have been selected mimic the protective carbohydrate epitopes, they could be expected to induce antibodies specific for the O—Ag of the S. flexneri LPS. The basic structure of the saccharidic unit, which is repeated to form the O—Ag of the S. flexneri species, is three rhamnose (Rha) and one N-acetylglucosamine (GlcNAc) with the presence of a glucosyl residue (Glc) that specifies the serotype. For instance, Glc linked to the central Rha residue specifies the serotype 5a (FIG. 1(a)), whereas Glc branched to the Rha linked to the GlcNAc specifies the serotype 2a (FIG. 1(b)). Usually, no anti-O—Ag antibodies specific for the serotype 2a are elicited following natural infection or experimental immunization with bacteria of the serotype 5a and vice-versa. As both mIgAs used for the selection of the peptide mimics are serotype 5a-specific, the peptide mimic-induced antibodies should therefore be specific for this serotype.

Figure 2A:
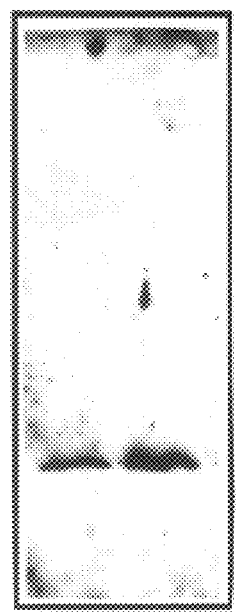
FIG. 2 shows the specificity of the peptide-induced antibodies. Western blots were performed using purified LPS of serotype 5a (lane 1) or serotype 2a (lane 2), and incubated with sera of mice (dilution 1:50) immunized with the phage clones pwt (a), p100c (b), p115 (c), or with mIgA C5 (dilution 1:1,000) (d).
Figure 2B:
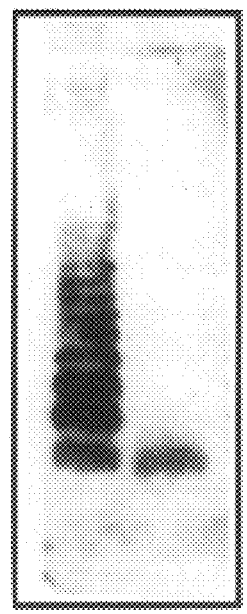
Figure 2C:
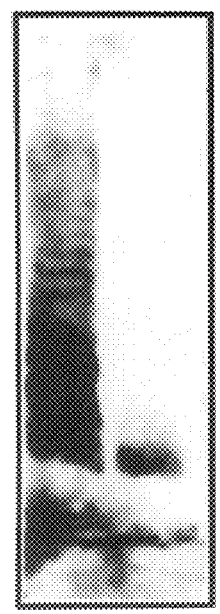
Figure 2D:
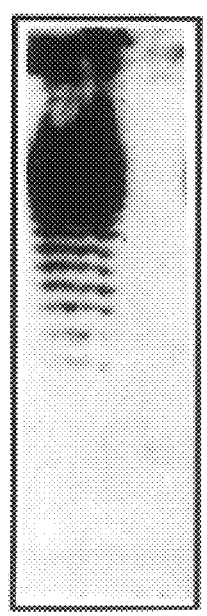

To test the immunogenicity of the peptide mimics, each of the 19 selected phage clones were used to immunize BALB/c mice as described above. The anti-carbohydrate antibody response induced was tested by immunoblotting using purified LPS from the S. flexneri serotypes 5a and 2a. Among the 19 clones previously selected, p100c (mIgA I3-specific) and p115 (recognized by both mIgAs), carrying the sequences YKPLGALTH (SEQ ID No. 1) and KVPP-WARTA (SEQ ID No. 2), respectively, induced anti-O—Ag antibodies that were specific for the serotype 5a (FIGS. 2(b) and (c) respectively). The observed ladder, which is a feature of the recognition of the O—Ag by specific antibodies, is constituted by the repeats of the basic saccharidic unit. Interestingly, the average molecular weight of the O—Ag molecules recognized by the peptide-induced antibodies was different from that of those recognized by mIgA C5 or mIgA I3 (FIG. 2d), which were used to select the immunogenic peptide mimics. The p100c- and p115-induced antibodies recognized O—Ag molecules of molecular weight ranging from 950 (1 unit) to 10,450 (11 units) (FIG. 2b), and from 950 (1 unit) to 16,150 (17 units) (FIG. 2c). A common pattern of recognition was similarly observed for mIgA C5 or I3, but these antibodies also recognized O—Ag molecules of higher molecular weight (FIG. 2d). The lowest band, corresponding to the LPS core moiety, was detected by the p100-c- and p15-induced antibodies (FIGS. 2, b and c, respectively) as well as by sera of mice immunized with pwt (FIG. 2a). As phage preparations may contain traces of E. coli LPS, whose core region is very similar to that of Shigella, the recognition of the S. flexneri core region probably reflected the cross-reactivity of anti-E. coli LPS antibodies induced following immunization with the phage particles.

EXAMPLE 3 p100c- and p115-induced Anti-LPS and Anti-phage Antibody Titers

Figure 3:
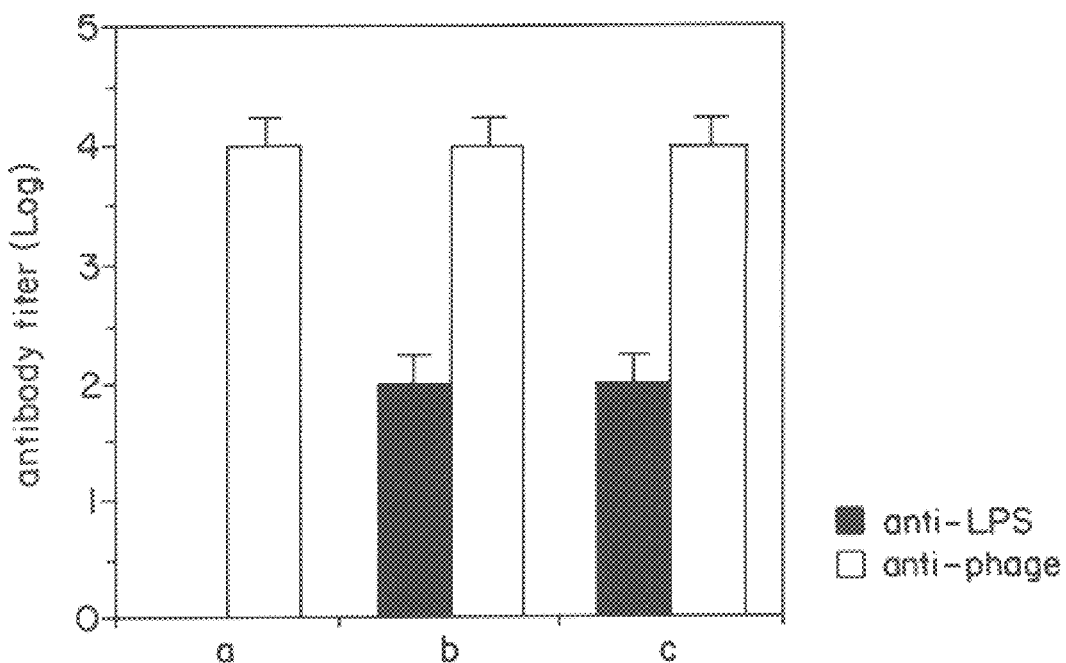
FIG. 3 shows p100c- and p115-induced anti-LPS and anti-phage antibody titers. Three groups of ten BALB/c mice were immunized i.p. with the phage clones pwt (a), p100c (b), or p115 (c) as described in Materials and Methods. Similar results were obtained following i.v. immunizations. The enzyme linked immunoassay (ELISA) data are representative of three independent experiments. Anti-LPS and anti-phage antibodies were estimated on individual sera. Titers are given as the mean ±SD of individual samples.

The antibody response induced by the two immunogenic peptide mimics was further analysed in ELISA. As immunizations were performed with the purified phage particles, the anti-LPS antibody response induced by p100c and p115 was mainly of the G isotype. As shown in FIG. 3(b and c), for both immunogenic mimics the anti-LPS and anti-phage antibody titers were 1:100 and 1:10,000, respectively. A similar anti-phage response was observed with the phage pwt (FIG. 3, a), whereas, as expected, no anti-LPS antibody response was detected.

Binding of the peptide mimic-induced antibodies to LPS in the presence of the phage clones p100c, p115, or pwt was also tested in ELISA. Inhibition of binding of p100c-induced antibodies was observed in the presence of p100c but not p115 or pwt. Similar results were obtained with p115 and the p115-induced antibodies (data not shown).

EXAMPLE 4

Figure 4A:
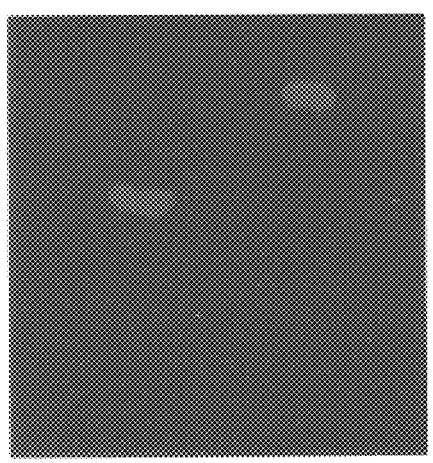
FIG. 4 shows the results of labeling of S. flexneri bacteria with the peptide mimic-induced antibodies. Labeling of S. flexneri serotype 5a (a) or serotype 2a (b) bacteria, previously centrifuged and fixed onto cover slips, was performed with sera of mice immunized with pwt, p100c, or p115. Goat anti-mouse rhodamine-conjugated immunoglobulin G was used as secondary antibody (dilution at use 1:200). Results shown in this Figure were obtained with p115-induced antibodies (dilution of sera at use 1:20) incubated with S. flexneri serotype 5a (a) or serotype 2a (b).
Figure 4B:
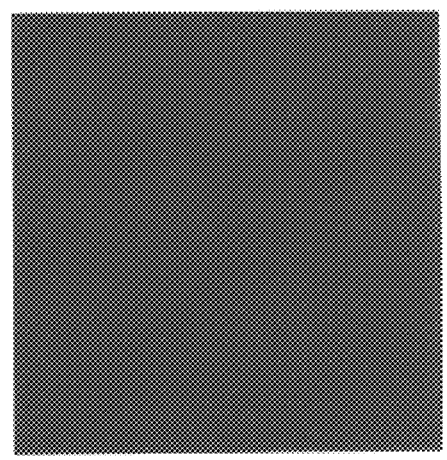

Recognition of S. flexneri serotype 5a Bacteria by Peptide Mimic-induced Antibodies If the antibodies play a role in protection against infection, thus disrupting the pathogenic process, they should recognize and bind to the bacteria. As could be expected, S. flexneri serotype 5a but not serotype 2a bacteria were recognized by p115-induced antibodies (FIG. 4, a and b). Similar data were obtained with p100c-induced antibodies (not shown). No labeling was observed when bacteria were incubated with pwt-induced antibodies (data not shown). These findings show that the peptide mimic-induced antibodies are able to interact with the pathogen in an in vivo situation.

EXAMPLE 5

Immunogenicity of the MAP Constructs

MAP-p100c and MAP-p115 were assayed by the ELISA technique for their binding capacity to the monoclonal antibodies mIgA C5 and mIgA I3 that have been used for selecting the p100c and p115 peptide mimics.

Only the MAP-p115 construct is recognized by the monoclonal antibodies. The failure of MAP-p100c to be recognized by the monoclonal antibodies may be explained in that the two cysteine residues flanking the peptide mimic have been removed in order to facilitate the synthesis of the MAP construct. These results suggest that the two cysteine residues are involved in the binding event with the monoclonal antibodies mIgA C5 and mIgA I3.

MAP-p115 is also recognized by the serum of mice immunized with the recombinant phage clones expressing the p115 polypeptide mimic. On the other hand, MAP-p115 is not recognized by the serum of mice immunized with an unrelated control phage.

Thus, the anti-peptide antibodies produced after immunization of mice with the p115 phage clones are able to bind to the peptide mimic outside the phage presentation environment when the antigen is presented to the cells via a MAP construct.

EXAMPLE 6

Protection Induced Following Immunization with 115/T/MAP

Protection against Shigella infection was assessed in mice previously immunized with the mimotopes as follows. Mice were immunized four times either intranasally (i.n.) with 100 micrograms of 115/T/MAP in the presence of 5 micrograms of cholera toxin (CT) or intraperitoneally (i.p.) with 100 micrograms of 115/T/MAP in the presence of alum. Control mice were immunized with T/MAP (100 micrograms per immunization) or wild type bacteria. For i.n. immunization, 106 live *S. flexneri* serotype 5a bacteria (M90T strain) were used. For i.p. immunization, $10^8$ killed *S. flexneri* serotype 5a bacteria (M90T strain) were used.

The antibody response was measured 15 days after the last immunization. The anti-LPS and the anti-peptide antibody titers were evaluated by ELISA using as antigen, purified LPS from the M90T strain and 115-KHL protein, respectively. The total serum Ig response is presented in FIG. 6.

FIG. 6 shows that higher anti-LPS or anti-peptide antibody titers were obtained for i.p. immunization with 115/T/MAP and the M90T strain. As expected, immunization with T/MAP did not elicit an antibody response. Interestingly, in addition to inducing anti-LPS antibodies, i.p. immunization with the M90T strain also induced antibodies that recognize peptide 115. In the anti-LPS antibody response, an approximately log difference was observed between mice immunized with 115/T/MAP and mice immunized with the M90T strain.

The protective capacity of the 115 mimotope-induced antibodies was assessed as follows. Immunized mice were challenged i.n. with $5 \times 10^7$ of the virulent bacteria. Lung-bacterial load was evaluated at 6 hours post infection. The results are presented in FIGS. 7 and 8. Mice immunized with 115/T/MAP had a reduced lung-bacterial load as compared to the group of mice immunized with T/MAP. Mice immunized with M90T exhibited a similar reduction in lung-bacterial load. Mice immunized i.p. with 115/T/MAP showed a significant reduction of the lung-bacterial load. (FIG. 7) The i.n. immunizations also showed a reduction of the lung-bacterial load in the 115/T/MAP-immunized mice; however, the results are not significant, due, perhaps, to the type of immunization, the level of antibodies induced, and the number of mice (5) per group (FIG. 8).

REFERENCES

Ada G. L. et al., Curr. Top. Microbiol. Immunol., 128:1–54.
Aguado et al., Immuno Biol., 184:113–125.
Austrian R. 1985. Polysaccharide vaccines.Ann.Inst.pasteur/Microbiol. 136B:295.
Banos D. M. et al., 1997, J. Virol., 71(1):419–426.
Barany F., 1911, Proc. Natl. Acad. Sci. USA, 88:189–193.
Beuvery E. C. et al., 1982, Infect. Immun., 37:15–22.
Beuvery et al., 1983, Infect. Immun., 41:609–617.
Bianchi E., A. Folgari, A. Wallace, M. Nicotra, S. Acali, A. Phalipon, G. Barbato, R. Bazzo, R. Cortese, F. Felici, and A. Pessi. 1995. A conformationnally homogeneous combinatorial peptide library. J Mol Biol. 247:154.
Bolmont et al., 1990, J. of Submicroscopic cytology and pathology, 22:117–122.
Bondada S., and M Garg. 1994. Thymus-independent antigens. In Handbook of B and T lymphocytes .E. C.Snow ed. Academic Press, p 343.
Bonnycastle L. L., J. S. Mehroke, M. Rashed, X. Gong, and J. K. Scott. 1996. Probing the basis of antibody reactivity with a panel of constrained peptide libraries displayed by filamentous phage. J Mol Biol. 258:747.
Bowie J. U. et al., 1990, Science, 47:1306–1310.
Cello J. et al., 1996, J. Gen. Virol., 77(Pt 9):2097–3108.
Chai H. et al., 1993, Biotechnol. Appl. Biochem., 18:259–273.
Cortese R., P. Monaci, A. Nicosia, A. Luzzago, F. Felici, F. Galfre, A. Pessi, A. Tramontano, and M. Sollazzo. 1995. Identification of biologically active peptides using random libraries displayed on phage. Curr. Opin. Biotechnol. 6:73.
Daniels D. A. and D. P. Lane. 1996. Phage peptide libraries. Methods 9:4940.
Dente L., G. Cesareni, G. Micheli, F. Felici, A. Folgori, A. Luzzago, P. Monaci, A. Nicosia, and P. Delmastro. 1994. Monoclonal antibodies that recognize filamentous phage: useful tools for phage display technology. Gene 148:7.
Duck P. et al., 1990, Biotechniques, 9:142–147.
DuPont H. L., Hornick R. B., Snyder M. J., Libonati J. P., Formal S. B., and E. J. Gangarosa. 1972. Immunity in shigellosis. II. Protection induced by oral live vaccine or primary infection. J. Inf. Dis. 125:12.
Ekwurzel G. et al., 1938, Publ. Hlth. Rep. (Wash), 53:1877–1893.
Felgner et al., 1987, Proc. Natl. Acad. Sci., 84:7413.
Felici F., A. Luzzago, P. Monaci, A. Nicosia, M. Sollazzo, and C. Traboni. 1995. Peptide and protein display on the surface of filamentous bacteriophage. In Biotechnology Annual Review Vol. 1. M. R. El-Gewely, ed Elsevier Science B. V. Amsterdam, The Netherlands, p. 149.
Felici F., G. Galfre, A. Luzzago, P. Monaci, A. Nicosia, and R. Cortese. 1996. Phage-displayed peptides as tools for the characterization of human sera. Meth. Enzymology. 267:116.
Felici F., L. Castagnoli, A. Musacchio, R. Japelli, and G. Cesareni. 1991. Selection of antibody ligands from a large library of oligopeptides expressed on a multivalent exposition vector. J. Mol. Biol. 222:301.
Fields B. A., F. A. Goldbaum, X. Ysern, R. Poljak and R. A. Mariuzza. 1995. Molecular basis of antigen mimicry by an anti-idiotope. Nature 374:739.
Fitzmaurice C. J. et al., Vaccine, 14(6):553–560.
Formal S. B., E. V. Oaks, R. E. Olsen, M. Wingfield-Eggleston, P. J. Snoy, and J. P. Cogan. 1991. Effect of prior infection with virulent Shigella flexneri 2a on the resistance of monkeys to subsequent infection with Shigella sonnei. J. Infect. Dis. 164:533.
Fraley et al., 1980, J. Biol. Chem., 255:10431
Francis T. J. et al., 1930, J. Exp. Med., 52:573–585.
Fuller S. A. et al., 1996, Immunology in Current Protocols in Molecular Biology, Ausubel et al. Eds, John Wiley & Sons, Inc., USA.
Graham S. et al., 1993, J. Virol., 67:1627–1637.
Guateli J. C. et al., 1990, Proc. Natl. Acad. Sci. USA, 87:1874–1878.
Heidelberger M. et al., 1948, J. Exp. Med., 88:369–372.
Henrickson K. J., 1991, J. Infect. Dis., 164:1128–1134.
Hoess R., U. Brinkmann, T. Handel, and I. Pastan. 1993. Identification of a peptide which binds to the carbohydrate-specific monoclonal antibody B3. Gene 128:43.

Hoshino Y. et al., 1984, J. Infect. Dis., 149:694–702.
Houbenweyl, 1974, in Meuthode der Organischen Chemie, E. Wunsch Ed., Volume 15-I et 15-II, Thieme, Stuttgart.
Huygen et al., 1996, Nature Medicine, 2(8):893–898.
Kaneda et al., 1989, Science, 243:375
Kasel J. A. et al., 1984, J. Virol., 52:828–832.
Kaufman P., 1947, Arch. Int. Med., 79:518–531.
Kayhty H. et al., 1984, Pediatrics, 74:857–865.
Kersten G. F. et al., 1995, Biochim. Biophys. Acta, 1241:117–138.
Kievitis T. et al., 1991, J. Virol. Methods, 35:273–286.
Koch Y., 1977, Biochem. Biophys. Res. Commun., 74:488–491.
Kwoh D. Y. et al., 1989, Proc. Natl. Acad. Sci. USA, 86:1173–1177.
Laemmli U. K. 1970. Cleavage of structural proteins during the assembly of the head of bacteriophage T4. Nature 227:680.
Landegren U. et al., 1988, Science, 241:1077–1080.
Lenhard T. et al., 1996, Gene, 169:187–190.
Lindberg A. A., A. Karnell, and A. Weintraub. 1991. The lipopolysaccharide of Shigella bacteria as a virulence factor. Rev. Infect. Diseases 13: S279.
Lovgren K. et al., 1988, Biotechnol. Appl. Biochem., 10:161–172.
Lucas A. H. 1994. New approaches to polysaccharide vaccines. In Development and clinical uses of Haemophilus b conjugate vaccines. R. W. Ellis, D. M. Granoff eds. Marcel Dekker Inc., p.455.
Luzzago A., F. Felici, A. Tramontano, A. Pessi, and R. Cortese. 1993. Mimicking of discontinuous epitopes by phage-displayed peptides, I. Epitope mapping of human ferritin using a phage library of constrained peptides. Gene 128:51.
Macleod C. et al., 1945, J. Exp/Med., 82:445–465.
Meloen R. H. and J. Briaire. 1980. A study of the cross-reacting antigens on the intact foot and mouth disease virus and its 12S subunits with antisera against the structural proteins. J. Gen. Virol. 51:107.
Menne S. et al., 1997, J. Virol., 71(1):65–74.
Merrifield, 1963, J. Am. Chem. Soc., 85:2149–2154.
Midoux, 1993, Nucleic Acids Research, 21:871–878
Morein B., 1990, Immunol. letters, 25:281–283.
Mounier J., F. K. Bahrani and P. J. Sansonetti. 1997. Secretion of Shigella flexneri Ipa Invasins upon contact with epithelial cells and subsequent entry of the bacteria into cells are growth-stage dependent. Infect. Immun.65:
Mowat A. M. et al., 1991, Immunol. Today, 12:383–385.
Murphy B. R. et al., 1990, Orthomyxoviruses, IN: Virology, B. N. Fields, D. M. Knipe, R. M. Chanock, M. S. Hirsch, and J. L. Melnick, eds, Raven, New York, 1091–1152.
Nisini R. et al., 1997, J. Virol., 71(3):2241–2251.
O'Reilly et al., 1992, Baculovirus expression vectors: a Laboratory Manual. W. H. Freeman and Co., New York.
Oaks E. V., Hale T. L. and S. B. Formal. 1986. Serum immune response to Shigella protein antigens in Rhesus monkeys and humans infected with Shigella spp. Infect. Immun. 53:57.
Oberhelman R. A., Kopecko D. J., Salazar-Lindo E., Gotuzzo E., Buysse J. M., Venkatesan M. M., Yi A., Fernandez-Prada C., Guzman M., Leon-Barua R. and R. B. Sack. 1991. Prospective study of systemic and mucosal immune responses in dysenteric patients to specific Shigella invasion plasmid antigens and lipopolysaccharide. Infect. Immun. 59:2341.
Oldenburg K. R., D. Loganathan, I. J. Goldstein, and P. G. Schultz. 1992. Peptide ligands for a sugar-binding protein isolated from a random peptide library. Proc .Natl. Acad Sci. 89:5393.
Pagano et al., 1967, J. Virol., 1:891.
Parmley S. F. and G. P. Smith.1988. Antibody-selectable filamentous fd phage vectors: affinity purification of target genes. Gene 73:305.
Pastore, 1994, Circulation, 90:I-517.
Phalipon A., Kaufmann M., Michetti P., Cavaillon J. M., Huerre M., Sansonetti P. J. and J. P. Kraehenbuhl. 1995. Monoclonal IgA antibody directed against serotype-specific epitope of Shigella flexneri lipopolysaccharide protects against murine experimental shigellosis. J. Exp. Med. 182:769.
Ray R. et al., 1986, Virology, 148:232–236.
Reiss E., 1986, Cell wall composition, In : Fungi pathogenic for humans and animals, Howard D. H. ed, Dekker, Basel, New York, Vol.3, part C, 57–101.
Rougeot, C., I. Rosinski-Chupin, E. Njamkepo, and F. Rougeon, 1994, Eur. J. Biochem. 219 (3): 765–773.
Sambrook, J. et al. 1989. In Molecular cloning: A Laboratory Manual. Cold Spring Harbor, N.Y.: Cold Spring Harbor Laboratory Press.
Sansonetti P. J. 1991. Genetic and molecular basis of epithelial cell invasion by Shigella species. Rev. Infect. Dis. 13: S285.
Schieman O. et al., 1927, Z. Hyg. Infekt.-Kr., 108:220–257.
Scott J. K. and L. Craig. 1994. Random peptide libraries. Curr. Opin. Biotechnol. 5:40.
Scott J. K., D. Loganathan, R. B. Easley, and X. Gong. 1992. A family of concanavalin A-binding peptides from a hexapeptide epitope library. Proc. Natl. Acad. Sci. 89:5398.
Segev D., 1992, in <<Non-radioactive Labeling and Detection of Biomolecules >>. Kessler C. Springer Verlag, Berlin, New-York, 197–205.
Senpuku H. et al., 1996, Immunology, 88(2):275–283.
Simons D. A. R. 1971. Immunochemistry of Shigella flexneri O-antigens: a study of structural and genetic aspects of the biosynthesis of cell-surface antigens. Bacteriol. reviews 35:117.
Smith et al., 1983, Mol. Cell. Biol., 3:2156–2165.
Smith G. P. and J. K. Scott. 1993. Libraries of peptides and proteins displayed on filamentous phage. Meth. Enzymol. 217:228.
Spargo C. A. et al., 1996, Mol. and Cell. Probes, 10:247–256
Tacson et al., 1996, Nature Medicine, 2(8):888–892.
Tam J. P., 1988, Proc. Natl. Acad. Sci., 85:5409–5413.
Tamura S-I. et al. 1990, Vaccine, 8:476–486.
Tamura S-I. et al., 1996, Intranasal immunization with Influenza vaccines, In: Mucosal vaccines, Kiyono H., Ogra P. L., and McGhee J. R. eds, Academic Press, 425–436.
Tamura S-I. et al., Eur. J. Immunol., 21, 1337–1344.
Tsurudome M. et al., 1989, Virology, 171:38–48.
Valadon P., G. Nussbaum, L. F. Boyd, D. H. Margulies, and M. D. Scharff. 1996. Peptide libraries define the fine specificity of anti-polysaccharide antibodies to Cryptococcus neoformans. J. Mol. Biol. 261:11.
Van Snick J. S. et al., 1986, Proc. Natl. Acad. Sci. USA, 83:9679–9683.
Vlasak R. et al., 1983, Eur. J. Biochem., 135:123–126.
Walker G. T. et al., 1992, Nucleic Acids Res., 20:1691–1696.
Westernick M. A. J., P. C. Giardina, M. A. Apicella, and T. Kieber-Emmons. 1995. Peptide mimicry of the meningococcal group C capsular polysaccharide. Proc. Natl. Acad. Sci. 92:4021.
Westphal O. and K. Jann. 1965. In Methods in Carbohydrate Chemistry, vol 5. R. L. Whistler and al. eds. Academic Press, New York, p 83.
Winner L. S., et al., 1991, Infect. Immun., 59:977–982.
Zamorano P. et al., 1995, Virology, 212(2):614–621.
Zhenlin et al., 1989, Gene, 78:243–254.

What is claimed is:

1. A purified immunogenic polypeptide comprising a polysaccharide mimotope recognized by a protective monoclonal antibody having a specificity for a surface polysaccharide of a bacterium of the Shigella species, said surface polysaccharide having said mimotope, wherein the polypeptide comprises the amino acid sequence of SEQ ID NO. 1: [R1-YKPLGATH-R2] R1-YKPLGALTH-R2, wherein R1 and R2 each represents either a cysteine residue or a hydrogen atom.

2. A purified immunogenic polypeptide comprising a polysaccharide mimotope recognized by a protective monoclonal antibody having a specificity for a surface polysaccharide of a bacterium of the Shigella species, said surface polysaccharide having said mimotope, wherein the polypeptide comprises the amino acid sequence of SEQ ID NO. 2: KVPPWAATA.

* * * * *

UNITED STATES PATENT AND TRADEMARK OFFICE
CERTIFICATE OF CORRECTION

PATENT NO.    : 6,528,061 B1
DATED         : March 4, 2003
INVENTOR(S)   : Armelle Phalipon et al.

It is certified that error appears in the above-identified patent and that said Letters Patent is hereby corrected as shown below:

Column 35,
Line 56, delete "[R1-YKPLGATH-R2]".

Signed and Sealed this

Fifteenth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,528,061 B1
DATED : March 4, 2003
INVENTOR(S) : Armelle Phalipon et al.

It is certified that error appears in the above-identified patent and that said Letters Patent is hereby corrected as shown below:

<u>Title page,</u>
Item [76], insert -- [73] Assignee: Institut Pasteur, Paris (FR) --.

Signed and Sealed this

Sixteenth Day of September, 2003

JAMES E. ROGAN
*Director of the United States Patent and Trademark Office*